US007223580B2

(12) United States Patent
Narimatsu et al.

(10) Patent No.: US 7,223,580 B2
(45) Date of Patent: May 29, 2007

(54) N-ACETYLGLUCOSAMINE TRANSFERASE, NUCLEIC ACID ENCODING THE SAME AND USE THEREOF IN DIAGNOSING CANCER AND/OR TUMOR

(75) Inventors: Hisashi Narimatsu, Tsukuba (JP); Niro Inaba, Tsukuba (JP); Akira Togayachi, Tsukuba (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 0 days.

(21) Appl. No.: 10/507,421

(22) PCT Filed: Mar. 14, 2003

(86) PCT No.: PCT/JP03/03044

§ 371 (c)(1),
(2), (4) Date: Mar. 11, 2005

(87) PCT Pub. No.: WO03/076624

PCT Pub. Date: Sep. 18, 2003

(65) Prior Publication Data

US 2005/0186570 A1    Aug. 25, 2005

(30) Foreign Application Priority Data

Mar. 14, 2002  (JP)  ............... 2002-070996

(51) Int. Cl.
| *C12N 9/10* | (2006.01) |
| *C12N 15/70* | (2006.01) |
| *C12N 5/16* | (2006.01) |
| *C12Q 1/68* | (2006.01) |
| *C12P 21/06* | (2006.01) |
| *C12P 19/04* | (2006.01) |
| *C07H 21/04* | (2006.01) |

(52) U.S. Cl. .................... 435/193; 435/6; 435/101; 435/183; 435/69.1; 435/320.1; 435/325; 536/23.2

(58) Field of Classification Search .................. 435/193
See application file for complete search history.

(56) References Cited

FOREIGN PATENT DOCUMENTS

| WO | WO-01/075067 A3 | 10/2001 |
| WO | WO 02/26950 A2 | 4/2002 |
| WO | WO-02/055683 A2 | 7/2002 |
| WO | WO-2004/039976 A1 | 5/2004 |

OTHER PUBLICATIONS

Akira Togayachi et al, Molecular cloning and characterization of UDP-GlcNAc: lactosylceramide beta 1,3-acetylglucosaminyltransferase (beta 3Gn-T5), an essential enzyme for the expression of HNK-1 and Lewis X epitopes on glycolipids. The Journal of Biological Chemistry, 2001, vol. 276, No. 25, pp. 22032 to 22040.

Norihiko Shiraishi, Identification and characterization of three novel beta 1,3-N-acetylglucosaminyltransferases structurally related to the beta 1,3-galactosyltransferase family. The Journal of Biological Chemistry, 2001, vol. 276, No. 5, pp. 3498 to 3507.
K. Sasaki et al., *Proc. Natl. Acad. Sci. USA*, vol. 94, pp. 14294-14299, Dec. 1997.
R. Kannagi, *Glycoconjugate Journal* (1997) 14: 577-584.
S. Nishihara et al., *The Journal of Biological Chemistry*, vol. 269, No. 46, pp. 29271-29278, Nov. 18, 1994.
C. Ohyama et al., *The EMBO Journal*, vol. 18, No. 6, pp. 1516-1525, 1999.
G. Wang et al., *Molecular Microbiology* (2000) 36(6) 1187-1196.
P. G. Falk et al., *Proc. Natl. Acad. Sci. USA*, vol. 92, pp. 1515-1519, Feb. 1995.
Iwai T et al: "Molecular cloning and characterization of a novel UDP-GlcNAc: GalNAc-pedptide β1, 3-N-acetylglucosaminyltransferase (β3Gn-T6), an enzyme synthesizing the core 3 structure of O-glycans" Journal of Biological Chemistry, vol. 277, No. 15, pp. 12802-12809, XP002961055 ISSN:0021-9258.
DATABASE EMBL 'Online! Dec. 14, 1999, "*Homo sapiens* BAC clone RP11-56215 from 2, complete sequence." XP002360645.
DATABASE Geneseq 'Online! Feb. 18, 2002, "Novel human diagnostic protein #20242." XP002360646.
DATABASE EMBL 'Online! Feb. 22, 2000, "*Homo sapiens* cDNA FLJ20763 fis, clone COL09911," XP002360648.
Kataoka K et al: "Screening for genes involved in tissue invasion based on placenta formation and cancer cell lines with low and high metastatic potential." vol. 163-, No. 2, Feb. 26, 2001, pp. 213-219, XP002360624.
DATABASE Geneseq 'Online! Jun. 26, 2001, "Human cDNA clone (5'-primer) SEQ ID No. 2089." XP002360649.
DATABASE EMBL 'Online! Jun. 25, 2002, "*Homo sapiens* beta 1, 3-N-acetylglucosaminyltransferase 7 mRNA, complete cds." XP002360650.
Ken Kataoka et al: "A novel β1, 3-N-acetylglucosaminyltransferase involved in invasion of cancer cells as assayed in vitro" Biochemical and Biophysical Research Communications, Academic Press, San Diego, CA, US, vol. 294, 2002, pp. 843-848, XP002975891 ISSN: 0006-291X.
DATABASE Geneseq 'Online! May 20, 2003, "Human NOV106a protein." XP002360651.

(Continued)

*Primary Examiner*—Manjunath N. Rao
*Assistant Examiner*—Iqbal Chowdhury
(74) *Attorney, Agent, or Firm*—Birch, Stewart, Kolasch & Birch, LLP

(57) ABSTRACT

An enzyme having an activity of transferring N-acetylglucosamine to the non-reducing end of a Galβ1-4Glc or Galβ1-4GlcNAc-group via a β-1,3 bond; a nucleic acid encoding the same; and a method of diagnosing cancer and/or tumor, in particular, digestive cancer and/or tumor using the expression dose of a gene of the above enzyme as an indication. A gene of a novel enzyme having an activity of transferring N-acetylglucosamine to the non-reducing end of a Gal β1-4Glc or Gal β1-4GlcNAc-group via a β-1,3 bond is cloned from human stomach cells and its base sequence is determined. Then this enzyme is expressed. Since this enzyme is scarcely or never produced in cancer and/or tumor, in particular, digestive cancer and/or tumor cells, cancer and/or tumor can be diagnosed with the use of the expression of the enzyme gene as an indication.

7 Claims, 2 Drawing Sheets

OTHER PUBLICATIONS

DATABASE Geneseq 'Online! May 20, 2003, "Human NOV106a cDNA." XP002360652.

DATABASE Geneseq 'Online! Feb. 26, 2003, "Human cDNA #848 differentially expressed in activated vascular tissue." XP002360653.

DATABASE EMBL 'Online! Feb. 3, 2004, "Sequence 23746 from Patent WO02068579." XP002360654.

DATABASE Geneseq 'Online! Nov. 4, 2004, "Amino acid sequence of human MAPCAX orthologue #5." XP002360655.

DATABASE Geneseq 'Online! Oct. 7, 2004, "Novel human protein sequence #1907." XP002360656.

DATABASE Geneseq 'Online! Feb. 12, 2004, "Human polypeptide sequence SEQ ID No. 1375." XP002360657.

DATABASE Geneseq 'Online! Feb. 12, 2004, "Human contig polypeptide sequence SEQ ID No. 2684." XP002360658.

DATABASE Geneseq 'Online! Feb. 12, 2004, "Human polynucleotide seqeucne SEQ ID No. 334." XP002360659.

DATABASE Geneseq 'Online! Feb. 12, 2004, "Human contig polynucleotide sequence SEQ ID No. 2232." XP002360660.

DATABASE Geneseq 'Online! Oct. 21, 2004, "Breast cancer prognosis marker #220." XP002360661.

Seko A et al: "β1, 3-N-Acetylglucosaminyltransferase-7 (β3Gn-T7) acts efficiently on keratan sulfate-related glycans" FEBS Letters, Elsevier, Amsterdam, NL, vol. 556, No. 1-3, Jan. 2, 2004, pp. 216-220, XP004483233 ISSN: 0014-5793.

DATABASE Geneseq 'Online! Feb. 13, 2002, DNA encoding novel human diagnostic protein #20242. XP002360647.

SEQUENCE LISTING

<160> NUMBER OF SEQ ID NOS: 28

<210> SEQ ID NO 1
<211> LENGTH: 283
<212> TYPE: PRT
<213> ORGANISM: Homo sapiens

<400> SEQUENCE: 1

Tyr Phe Pro Met Leu Leu Asn His Pro Glu Lys Cys Arg Gly Asp Val
 1               5                  10                  15

Tyr Leu Leu Val Val Val Lys Ser Val Ile Thr Gln His Asp Arg Arg
            20                  25                  30

Glu Ala Ile Arg Gln Thr Trp Gly Arg Glu Arg Gln Ser Ala Gly Gly
        35                  40                  45

Gly Arg Gly Ala Val Arg Thr Leu Phe Leu Leu Gly Thr Ala Ser Lys
    50                  55                  60

Gln Glu Glu Arg Thr His Tyr Gln Gln Leu Leu Ala Tyr Glu Asp Arg
65                  70                  75                  80

Leu Tyr Gly Asp Ile Leu Gln Trp Gly Phe Leu Asp Thr Phe Phe Asn
                85                  90                  95

Leu Thr Leu Lys Glu Ile His Phe Leu Lys Trp Leu Asp Ile Tyr Cys
            100                 105                 110

Pro His Val Pro Phe Ile Phe Lys Gly Asp Asp Asp Val Phe Val Asn
        115                 120                 125

Pro Thr Asn Leu Leu Glu Phe Leu Ala Asp Arg Gln Pro Gln Glu Asn
    130                 135                 140

-continued

```
Leu Phe Val Gly Asp Val Leu Gln His Ala Arg Pro Ile Arg Arg Lys
145                 150                 155                 160

Asp Asn Lys Tyr Tyr Ile Pro Gly Ala Leu Tyr Gly Lys Ala Ser Tyr
                165                 170                 175

Pro Pro Tyr Ala Gly Gly Gly Phe Leu Met Ala Gly Ser Leu Ala
            180                 185                 190

Arg Arg Leu His His Ala Cys Asp Thr Leu Glu Leu Tyr Pro Ile Asp
            195                 200                 205

Asp Val Phe Leu Gly Met Cys Leu Glu Val Leu Gly Val Gln Pro Thr
        210                 215                 220

Ala His Glu Gly Phe Lys Thr Phe Gly Ile Ser Arg Asn Arg Asn Ser
225                 230                 235                 240

Arg Met Asn Lys Glu Pro Cys Phe Phe Arg Ala Met Leu Val Val His
                245                 250                 255

Lys Leu Leu Pro Pro Glu Leu Leu Ala Met Trp Gly Leu Val His Ser
            260                 265                 270

Asn Leu Thr Cys Ser Arg Lys Leu Gln Val Leu
            275                 280
```

<210> SEQ ID NO 2
<211> LENGTH: 849
<212> TYPE: DNA
<213> ORGANISM: Homo sapiens

<400> SEQUENCE: 2

```
tac ttc ccc atg ctg ctg aac cac ccg gag aag tgc agg ggc gat gtc      48
Tyr Phe Pro Met Leu Leu Asn His Pro Glu Lys Cys Arg Gly Asp Val
  1               5                  10                  15 tac ctg ctg gtg gtt gtc aag tcg gtc atc acg cag cac gac cgc cgc      96
Tyr Leu Leu Val Val Val Lys Ser Val Ile Thr Gln His Asp Arg Arg
             20                  25                  30 gag gcc atc cgc cag acc tgg ggc cgc gag cgg cag tcc gcg ggt ggg     144
Glu Ala Ile Arg Gln Thr Trp Gly Arg Glu Arg Gln Ser Ala Gly Gly
         35                  40                  45 ggc cga ggc gcc gtg cgc acc ctc ttc ctg ctg ggc acg gcc tcc aag     192
Gly Arg Gly Ala Val Arg Thr Leu Phe Leu Leu Gly Thr Ala Ser Lys
     50                  55                  60 cag gag gag cgc acg cac tac cag cag ctg ctg gcc tac gaa gac cgc     240
Gln Glu Glu Arg Thr His Tyr Gln Gln Leu Leu Ala Tyr Glu Asp Arg
 65                  70                  75                  80 ctc tac ggc gac atc ctg cag tgg ggc ttt ctc gac acc ttc ttc aac     288
Leu Tyr Gly Asp Ile Leu Gln Trp Gly Phe Leu Asp Thr Phe Phe Asn
                 85                  90                  95 ctg acc ctc aag gag atc cac ttc ctc aag tgg ctg gac atc tac tgc     336
Leu Thr Leu Lys Glu Ile His Phe Leu Lys Trp Leu Asp Ile Tyr Cys
            100                 105                 110 ccc cac gtc ccc ttc att ttc aaa ggc gac gat gac gtc ttc gtc aac     384
Pro His Val Pro Phe Ile Phe Lys Gly Asp Asp Asp Val Phe Val Asn
        115                 120                 125 ccc acc aac ctg cta gaa ttt ctg gct gac cgg cag cca cag gaa aac     432
Pro Thr Asn Leu Leu Glu Phe Leu Ala Asp Arg Gln Pro Gln Glu Asn
    130                 135                 140 ctg ttc gtg ggc gat gtc ctg cag cac gct cgg ccc att cgc agg aaa     480
Leu Phe Val Gly Asp Val Leu Gln His Ala Arg Pro Ile Arg Arg Lys
145                 150                 155                 160 gac aac aaa tac tac atc ccg ggg gcc ctg tac ggc aag gcc agc tat     528
Asp Asn Lys Tyr Tyr Ile Pro Gly Ala Leu Tyr Gly Lys Ala Ser Tyr
                165                 170                 175
```

-continued

```
ccg ccg tat gca ggc ggc ggt ggc ttc ctc atg gcc ggc agc ctg gcc      576
Pro Pro Tyr Ala Gly Gly Gly Gly Phe Leu Met Ala Gly Ser Leu Ala
            180                 185                 190 cgg cgc ctg cac cat gcc tgc gac acc ctg gag ctc tac ccg atc gac      624
Arg Arg Leu His His Ala Cys Asp Thr Leu Glu Leu Tyr Pro Ile Asp
        195                 200                 205 gac gtc ttt ctg ggc atg tgc ctg gag gtg ctg ggc gtg cag ccc acg      672
Asp Val Phe Leu Gly Met Cys Leu Glu Val Leu Gly Val Gln Pro Thr
    210                 215                 220 gcc cac gag ggc ttc aag act ttc ggc atc tcc cgg aac cgc aac agc      720
Ala His Glu Gly Phe Lys Thr Phe Gly Ile Ser Arg Asn Arg Asn Ser
225                 230                 235                 240 cgc atg aac aag gag ccg tgc ttt ttc cgc gcc atg ctc gtg gtg cac      768
Arg Met Asn Lys Glu Pro Cys Phe Phe Arg Ala Met Leu Val Val His
                245                 250                 255 aag ctg ctg ccc cct gag ctg ctc gcc atg tgg ggc ctg gtg cac agc      816
Lys Leu Leu Pro Pro Glu Leu Leu Ala Met Trp Gly Leu Val His Ser
            260                 265                 270 aat ctc acc tgc tcc cgc aag ctc cag gtg ctc                          849
Asn Leu Thr Cys Ser Arg Lys Leu Gln Val Leu
        275                 280
```

<210> SEQ ID NO 3
<211> LENGTH: 327
<212> TYPE: PRT
<213> ORGANISM: Homo sapiens

<400> SEQUENCE: 3

```
Ala Ser Gln Gly Pro Gln Ala Trp Asp Val Thr Thr Thr Asn Cys Ser
1               5                   10                  15

Ala Asn Ile Asn Leu Thr His Gln Pro Trp Phe Gln Val Leu Glu Pro
            20                  25                  30

Gln Phe Arg Gln Phe Leu Phe Tyr Arg His Cys Arg Tyr Phe Pro Met
        35                  40                  45

Leu Leu Asn His Pro Glu Lys Cys Arg Gly Asp Val Tyr Leu Leu Val
    50                  55                  60

Val Val Lys Ser Val Ile Thr Gln His Asp Arg Arg Glu Ala Ile Arg
65                  70                  75                  80

Gln Thr Trp Gly Arg Glu Arg Gln Ser Ala Gly Gly Arg Gly Ala
                85                  90                  95

Val Arg Thr Leu Phe Leu Leu Gly Thr Ala Ser Lys Gln Glu Glu Arg
            100                 105                 110

Thr His Tyr Gln Gln Leu Leu Ala Tyr Glu Asp Arg Leu Tyr Gly Asp
        115                 120                 125

Ile Leu Gln Trp Gly Phe Leu Asp Thr Phe Phe Asn Leu Thr Leu Lys
    130                 135                 140

Glu Ile His Phe Leu Lys Trp Leu Asp Ile Tyr Cys Pro His Val Pro
145                 150                 155                 160

Phe Ile Phe Lys Gly Asp Asp Val Phe Val Asn Pro Thr Asn Leu
                165                 170                 175

Leu Glu Phe Leu Ala Asp Arg Gln Pro Gln Glu Asn Leu Phe Val Gly
            180                 185                 190

Asp Val Leu Gln His Ala Arg Pro Ile Arg Arg Lys Asp Asn Lys Tyr
        195                 200                 205

Tyr Ile Pro Gly Ala Leu Tyr Gly Lys Ala Ser Tyr Pro Pro Tyr Ala
    210                 215                 220
```

```
Gly Gly Gly Gly Phe Leu Met Ala Gly Ser Leu Ala Arg Arg Leu His
225                 230                 235                 240

His Ala Cys Asp Thr Leu Glu Leu Tyr Pro Ile Asp Asp Val Phe Leu
            245                 250                 255

Gly Met Cys Leu Glu Val Leu Gly Val Gln Pro Thr Ala His Glu Gly
        260                 265                 270

Phe Lys Thr Phe Gly Ile Ser Arg Asn Arg Asn Ser Arg Met Asn Lys
    275                 280                 285

Glu Pro Cys Phe Phe Arg Ala Met Leu Val Val His Lys Leu Leu Pro
290                 295                 300

Pro Glu Leu Leu Ala Met Trp Gly Leu Val His Ser Asn Leu Thr Cys
305                 310                 315                 320

Ser Arg Lys Leu Gln Val Leu
                325

<210> SEQ ID NO 4
<211> LENGTH: 981
<212> TYPE: DNA
<213> ORGANISM: Homo sapiens

<400> SEQUENCE: 4
```

| | | | | | | | | | | | | | | | | |
|---|---|---|---|---|---|---|---|---|---|---|---|---|---|---|---|---|
| gcc | tct | cag | ggg | ccc | cag | gcc | tgg | gac | gtg | acc | acc | act | aac | tgc | tca | 48 |
| Ala | Ser | Gln | Gly | Pro | Gln | Ala | Trp | Asp | Val | Thr | Thr | Thr | Asn | Cys | Ser | |
| 1 | | | | 5 | | | | | 10 | | | | | 15 | | |
| gcc | aat | atc | aac | ttg | acc | cac | cag | ccc | tgg | ttc | cag | gtc | ctg | gag | ccg | 96 |
| Ala | Asn | Ile | Asn | Leu | Thr | His | Gln | Pro | Trp | Phe | Gln | Val | Leu | Glu | Pro | |
| | | | 20 | | | | | 25 | | | | | 30 | | | |
| cag | ttc | cgg | cag | ttt | ctc | ttc | tac | cgc | cac | tgc | cgc | tac | ttc | ccc | atg | 144 |
| Gln | Phe | Arg | Gln | Phe | Leu | Phe | Tyr | Arg | His | Cys | Arg | Tyr | Phe | Pro | Met | |
| | | 35 | | | | | 40 | | | | | 45 | | | | |
| ctg | ctg | aac | cac | ccg | gag | aag | tgc | agg | ggc | gat | gtc | tac | ctg | ctg | gtg | 192 |
| Leu | Leu | Asn | His | Pro | Glu | Lys | Cys | Arg | Gly | Asp | Val | Tyr | Leu | Leu | Val | |
| | 50 | | | | | 55 | | | | | 60 | | | | | |
| gtt | gtc | aag | tcg | gtc | atc | acg | cag | cac | gac | cgc | cgc | gag | gcc | atc | cgc | 240 |
| Val | Val | Lys | Ser | Val | Ile | Thr | Gln | His | Asp | Arg | Arg | Glu | Ala | Ile | Arg | |
| 65 | | | | 70 | | | | | 75 | | | | | 80 | | |
| cag | acc | tgg | ggc | cgc | gag | cgg | cag | tcc | gcg | ggt | ggg | ggc | cga | ggc | gcc | 288 |
| Gln | Thr | Trp | Gly | Arg | Glu | Arg | Gln | Ser | Ala | Gly | Gly | Gly | Arg | Gly | Ala | |
| | | | 85 | | | | | 90 | | | | | 95 | | | |
| gtg | cgc | acc | ctc | ttc | ctg | ctg | ggc | acg | gcc | tcc | aag | cag | gag | gag | cgc | 336 |
| Val | Arg | Thr | Leu | Phe | Leu | Leu | Gly | Thr | Ala | Ser | Lys | Gln | Glu | Glu | Arg | |
| | | | 100 | | | | | 105 | | | | | 110 | | | |
| acg | cac | tac | cag | cag | ctg | ctg | gcc | tac | gaa | gac | cgc | ctc | tac | ggc | gac | 384 |
| Thr | His | Tyr | Gln | Gln | Leu | Leu | Ala | Tyr | Glu | Asp | Arg | Leu | Tyr | Gly | Asp | |
| | | 115 | | | | | 120 | | | | | 125 | | | | |
| atc | ctg | cag | tgg | ggc | ttt | ctc | gac | acc | ttc | ttc | aac | ctg | acc | ctc | aag | 432 |
| Ile | Leu | Gln | Trp | Gly | Phe | Leu | Asp | Thr | Phe | Phe | Asn | Leu | Thr | Leu | Lys | |
| | 130 | | | | | 135 | | | | | 140 | | | | | |
| gag | atc | cac | ttc | ctc | aag | tgg | ctg | gac | atc | tac | tgc | ccc | cac | gtc | ccc | 480 |
| Glu | Ile | His | Phe | Leu | Lys | Trp | Leu | Asp | Ile | Tyr | Cys | Pro | His | Val | Pro | |
| 145 | | | | 150 | | | | | 155 | | | | | 160 | | |
| ttc | att | ttc | aaa | ggc | gac | gat | gac | gtc | ttc | gtc | aac | ccc | acc | aac | ctg | 528 |
| Phe | Ile | Phe | Lys | Gly | Asp | Asp | Asp | Val | Phe | Val | Asn | Pro | Thr | Asn | Leu | |
| | | | 165 | | | | | 170 | | | | | 175 | | | |
| cta | gaa | ttt | ctg | gct | gac | cgg | cag | cca | cag | gaa | aac | ctg | ttc | gtg | ggc | 576 |
| Leu | Glu | Phe | Leu | Ala | Asp | Arg | Gln | Pro | Gln | Glu | Asn | Leu | Phe | Val | Gly | |
| | | | 180 | | | | | 185 | | | | | 190 | | | |

```
gat gtc ctg cag cac gct cgg ccc att cgc agg aaa gac aac aaa tac    624
Asp Val Leu Gln His Ala Arg Pro Ile Arg Arg Lys Asp Asn Lys Tyr
            195                 200                 205 tac atc ccg ggg gcc ctg tac ggc aag gcc agc tat ccg ccg tat gca    672
Tyr Ile Pro Gly Ala Leu Tyr Gly Lys Ala Ser Tyr Pro Pro Tyr Ala
        210                 215                 220 ggc ggc ggt ggc ttc ctc atg gcc ggc agc ctg gcc cgg cgc ctg cac    720
Gly Gly Gly Gly Phe Leu Met Ala Gly Ser Leu Ala Arg Arg Leu His
225                 230                 235                 240 cat gcc tgc gac acc ctg gag ctc tac ccg atc gac gac gtc ttt ctg    768
His Ala Cys Asp Thr Leu Glu Leu Tyr Pro Ile Asp Asp Val Phe Leu
                245                 250                 255 ggc atg tgc ctg gag gtg ctg ggc gtg cag ccc acg gcc cac gag ggc    816
Gly Met Cys Leu Glu Val Leu Gly Val Gln Pro Thr Ala His Glu Gly
            260                 265                 270 ttc aag act ttc ggc atc tcc cgg aac cgc aac agc cgc atg aac aag    864
Phe Lys Thr Phe Gly Ile Ser Arg Asn Arg Asn Ser Arg Met Asn Lys
        275                 280                 285 gag ccg tgc ttt ttc cgc gcc atg ctc gtg gtg cac aag ctg ctg ccc    912
Glu Pro Cys Phe Phe Arg Ala Met Leu Val Val His Lys Leu Leu Pro
290                 295                 300 cct gag ctg ctc gcc atg tgg ggg ctg gtg cac agc aat ctc acc tgc    960
Pro Glu Leu Leu Ala Met Trp Gly Leu Val His Ser Asn Leu Thr Cys
305                 310                 315                 320 tcc cgc aag ctc cag gtg ctc                                        981
Ser Arg Lys Leu Gln Val Leu
                325

<210> SEQ ID NO 5
<211> LENGTH: 1206
<212> TYPE: DNA
<213> ORGANISM: Homo sapiens

<400> SEQUENCE: 5 atg tcg ctg tgg aag aaa acc gtc tac cgg agt ctg tgc ctg gcc ctg     48
Met Ser Leu Trp Lys Lys Thr Val Tyr Arg Ser Leu Cys Leu Ala Leu
1               5                   10                  15 gcc ctg ctc gtg gcc gtg acg gtg ttc caa cgc agt ctc acc cct ggt     96
Ala Leu Leu Val Ala Val Thr Val Phe Gln Arg Ser Leu Thr Pro Gly
            20                  25                  30 cag ttt ctg cag gag cct ccg cca ccc acc ctg gag cca cag aag gcc    144
Gln Phe Leu Gln Glu Pro Pro Pro Pro Thr Leu Glu Pro Gln Lys Ala
        35                  40                  45 cag aag cca aat gga cag ctg gtg aac ccc aac aac ttc tgg aag aac    192
Gln Lys Pro Asn Gly Gln Leu Val Asn Pro Asn Asn Phe Trp Lys Asn
    50                  55                  60 ccg aaa gat gtg gct gcg ccc acg ccc atg gcc tct cag ggg ccc cag    240
Pro Lys Asp Val Ala Ala Pro Thr Pro Met Ala Ser Gln Gly Pro Gln
65                  70                  75                  80 gcc tgg gac gtg acc acc act aac tgc tca gcc aat atc aac ttg acc    288
Ala Trp Asp Val Thr Thr Thr Asn Cys Ser Ala Asn Ile Asn Leu Thr
                85                  90                  95 cac cag ccc tgg ttc cag gtc ctg gag ccg cag ttc cgg cag ttt ctc    336
His Gln Pro Trp Phe Gln Val Leu Glu Pro Gln Phe Arg Gln Phe Leu
            100                 105                 110 ttc tac cgc cac tgc cgc tac ttc ccc atg ctg ctg aac cac ccg gag    384
Phe Tyr Arg His Cys Arg Tyr Phe Pro Met Leu Leu Asn His Pro Glu
        115                 120                 125 aag tgc agg ggc gat gtc tac ctg ctg gtg gtt gtc aag tcg gtc atc    432
Lys Cys Arg Gly Asp Val Tyr Leu Leu Val Val Val Lys Ser Val Ile
    130                 135                 140
```

-continued

```
acg cag cac gac cgc cgc gag gcc atc cgc cag acc tgg ggc cgc gag    480
Thr Gln His Asp Arg Arg Glu Ala Ile Arg Gln Thr Trp Gly Arg Glu
145                 150                 155                 160 cgg cag tcc gcg ggt ggg ggc cga ggc gcc gtg cgc acc ctc ttc ctg    528
Arg Gln Ser Ala Gly Gly Gly Arg Gly Ala Val Arg Thr Leu Phe Leu
                165                 170                 175 ctg ggc acg gcc tcc aag cag gag gag cgc acg cac tac cag cag ctg    576
Leu Gly Thr Ala Ser Lys Gln Glu Glu Arg Thr His Tyr Gln Gln Leu
            180                 185                 190 ctg gcc tac gaa gac cgc ctc tac ggc gac atc ctg cag tgg ggc ttt    624
Leu Ala Tyr Glu Asp Arg Leu Tyr Gly Asp Ile Leu Gln Trp Gly Phe
        195                 200                 205 ctc gac acc ttc ttc aac ctg acc ctc aag gag atc cac ttc ctc aag    672
Leu Asp Thr Phe Phe Asn Leu Thr Leu Lys Glu Ile His Phe Leu Lys
    210                 215                 220 tgg ctg gac atc tac tgc ccc cac gtc ccc ttc att ttc aaa ggc gac    720
Trp Leu Asp Ile Tyr Cys Pro His Val Pro Phe Ile Phe Lys Gly Asp
225                 230                 235                 240 gat gac gtc ttc gtc aac ccc acc aac ctg cta gaa ttt ctg gct gac    768
Asp Asp Val Phe Val Asn Pro Thr Asn Leu Leu Glu Phe Leu Ala Asp
                245                 250                 255 cgg cag cca cag gaa aac ctg ttc gtg ggc gat gtc ctg cag cac gct    816
Arg Gln Pro Gln Glu Asn Leu Phe Val Gly Asp Val Leu Gln His Ala
            260                 265                 270 cgg ccc att cgc agg aaa gac aac aaa tac tac atc ccg ggg gcc ctg    864
Arg Pro Ile Arg Arg Lys Asp Asn Lys Tyr Tyr Ile Pro Gly Ala Leu
        275                 280                 285 tac ggc aag gcc agc tat ccg ccg tat gca ggc ggt ggc ttc ctc        912
Tyr Gly Lys Ala Ser Tyr Pro Pro Tyr Ala Gly Gly Gly Phe Leu
    290                 295                 300 atg gcc ggc agc ctg gcc cgg cgc ctg cac cat gcc tgc gac acc ctg    960
Met Ala Gly Ser Leu Ala Arg Arg Leu His His Ala Cys Asp Thr Leu
305                 310                 315                 320 gag ctc tac ccg atc gac gac gtc ttt ctg ggc atg tgc ctg gag gtg   1008
Glu Leu Tyr Pro Ile Asp Asp Val Phe Leu Gly Met Cys Leu Glu Val
                325                 330                 335 ctg ggc gtg cag ccc acg gcc cac gag ggc ttc aag act ttc ggc atc   1056
Leu Gly Val Gln Pro Thr Ala His Glu Gly Phe Lys Thr Phe Gly Ile
            340                 345                 350 tcc cgg aac cgc aac agc cgc atg aac aag gag ccg tgc ttt ttc cgc   1104
Ser Arg Asn Arg Asn Ser Arg Met Asn Lys Glu Pro Cys Phe Phe Arg
        355                 360                 365 gcc atg ctc gtg gtg cac aag ctg ctg ccc cct gag ctg ctc gcc atg   1152
Ala Met Leu Val Val His Lys Leu Leu Pro Pro Glu Leu Leu Ala Met
    370                 375                 380 tgg ggg ctg gtg cac agc aat ctc acc tgc tcc cgc aag ctc cag gtg   1200
Trp Gly Leu Val His Ser Asn Leu Thr Cys Ser Arg Lys Leu Gln Val
385                 390                 395                 400 ctc tga                                                           1206
Leu
```

<210> SEQ ID NO 6
<211> LENGTH: 2228
<212> TYPE: DNA
<213> ORGANISM: Homo sapiens

<400> SEQUENCE: 6

```
cccagggcct cgccgccttc ccggtgcacc ccccgacctc ccccgtcccg gcctcggtgg     60
gcggcttccc tggaaccct agggctggca gggccggatc cggagccctc cgtttcctcc    120
```

-continued

```
ccggagagct ggaccttggg tcacaccccc cagcctgcac ctaaggtgcc cctgtcttcc      180
tccaaccaca tgccccagca acctggggac cctatgggga aaatgtcgct ctatggggct      240
cagcctgcat tcaccctggg gcctggacct gcaaccggac cagccctcag ggcaacccag      300
gcgtctccac gggctgcctg tctctcctgg caccctgctc ctcccccttg gaggtcagcg      360
ccatctctct gctaggctgg ccctggaagg ccactctgct gtcccagag ctctcagccc       420 ccaggtctcc actggggagg gtgggcagg tgtcctggca gccccggag ggtgagatga        480 agagaggagg tccttcagga caggggctca ggccccaggg cttgggacga ccagcactcc      540
tggcagagag ctctaatttc tgcttccgaa atgggtgtgg accgggggttg gggtgggggg      600 gtctctgggc aagaagggtc cctcaagggc tggagctgca aatgtgcccc ctcccaggga      660
gtagagctgt agcctcatgt cttctaatgg ggtgttatga gctggggatg ttaaggtagg      720
ggtgaggggc agtgccatgc tagaggtgct cactgcatcc ttgggcctcc atcaaccatg      780
agggctgctc tttgttgggt gagacagact ggagaagggg gaggagggcc agtcttcctc      840
aggtcccaag ctcgagccac tctccaatgt gccccacatg tgatggagct cccgggcggc      900
acagaggatc agagggtgcc ctctcaatga ctctggctct gagtcaccta atgataccga      960
tacctactgc tgtgggtagg tacaccgcag ggaaatgaaa ggcattgggg ttccaggcgt     1020 gggaacagg gcagaggttt ccacctgagg ccctcctgtt aaggtgacag cattccccta     1080
actgtgcacc cgctgcctgg tactttatat agcactccaa tcctgtgttt tagccccatt     1140
tgggggaaga agaaatcgtg gctcagagtg gttgtaaacc actcattcag cttgtaagcg     1200
tcagggcctg attccacagt gctccttgag gagagggcag ggtgggagaa agaaagggca     1260
gggtgggaga ggaagcggga ccctaccctg acagcttagg gactccggga ctgagcctgt     1320
gcccaggtcc acttgcccgt ctgggaccac ccagcctccc aagggggggcg ccaggagagc     1380 cctgggctca tcttttctct ctcctctgta ctgtccgctc tccccacag gaagaaaacc      1440 gtctaccgga gtctgtgcct ggccctggcc ctgctcgtgg ccgtgacggt gttccaacgc     1500
agtctcaccc ctggtcagtt tctgcaggag cctccgccac ccaccctgga gccacagaag     1560
gcccagaagc caaatggaca gctggtgaac cccaacaact tctggaagaa cccgaaagat     1620
```

| gtggctgcgc ccacgccc atg gcc tct cag ggg ccc cag gcc tgg gac gtg | 1671 |
|---|---|
|                           Met Ala Ser Gln Gly Pro Gln Ala Trp Asp Val | |
|                           1            5                   10 | |
| acc act act aac tgc tca gcc aat atc aac ttg acc cac cag ccc tgg | 1719 |
| Thr Thr Thr Asn Cys Ser Ala Asn Ile Asn Leu Thr His Gln Pro Trp | |
|              15                   20                  25 | |
| ttc cag gtc ctg gag ccg cag ttc cgg cag ttt ctc ttc tac cgc cac | 1767 |
| Phe Gln Val Leu Glu Pro Gln Phe Arg Gln Phe Leu Phe Tyr Arg His | |
|         30                   35                  40 | |
| tgc cgc tac ttc ccc atg ctg ctg aac cac ccg gag aag tgc agg ggc | 1815 |
| Cys Arg Tyr Phe Pro Met Leu Leu Asn His Pro Glu Lys Cys Arg Gly | |
|      45                   50                  55 | |
| gat gtc tac ctg ctg gtg gtt gtc aag tcg gtc atc acg cag cac gac | 1863 |
| Asp Val Tyr Leu Leu Val Val Val Lys Ser Val Ile Thr Gln His Asp | |
| 60                  65                   70                  75 | |
| cgc cgc gag gcc atc cgc cag acc tgg ggc cgc gag cgg cag tcc gcg | 1911 |
| Arg Arg Glu Ala Ile Arg Gln Thr Trp Gly Arg Glu Arg Gln Ser Ala | |
|              80                   85                  90 | |
| ggt ggg ggc cga ggc gcc gtg cgc acc ctc ttc ctg ctg ggc acg gcc | 1959 |
| Gly Gly Gly Arg Gly Ala Val Arg Thr Leu Phe Leu Leu Gly Thr Ala | |
|      95                   100                105 | |

-continued

```
tcc aag cag gag gag cgc acg cac tac cag cag ctg ctg gcc tac gaa      2007
Ser Lys Gln Glu Glu Arg Thr His Tyr Gln Gln Leu Leu Ala Tyr Glu
    110                 115                 120 gac cgc ctc tac ggc gac atc ctg cag tgg ggc ttt ctc gac acc ttc      2055
Asp Arg Leu Tyr Gly Asp Ile Leu Gln Trp Gly Phe Leu Asp Thr Phe
125                 130                 135 ttc aac ctg acc ctc aag gag atc cac ttc ctc aag tgg ctg gac atc      2103
Phe Asn Leu Thr Leu Lys Glu Ile His Phe Leu Lys Trp Leu Asp Ile
140                 145                 150                 155 tac tgc ccc cac gtc ccc ttc att ttc aaa ggc gac gat gac gtc ttc      2151
Tyr Cys Pro His Val Pro Phe Ile Phe Lys Gly Asp Asp Asp Val Phe
                160                 165                 170 gtc aac ccc acc aac ctg cta gaa ttt ctg gct gac cgg cag cca cag      2199
Val Asn Pro Thr Asn Leu Leu Glu Phe Leu Ala Asp Arg Gln Pro Gln
            175                 180                 185 gaa aac ctg ttc gtg ggc gat gtc ctg ca                               2228
Glu Asn Leu Phe Val Gly Asp Val Leu
        190                 195

<210> SEQ ID NO 7
<211> LENGTH: 848
<212> TYPE: DNA
<213> ORGANISM: Homo sapiens

<400> SEQUENCE: 7 cag cag ctg ctg gcc tac gaa gac cgc ctc tac ggc gac atc ctg cag       48
Gln Gln Leu Leu Ala Tyr Glu Asp Arg Leu Tyr Gly Asp Ile Leu Gln
1               5                  10                  15 tgg ggc ttt ctc gac acc ttc ttc aac ctg acc ctc aag gag atc cac       96
Trp Gly Phe Leu Asp Thr Phe Phe Asn Leu Thr Leu Lys Glu Ile His
            20                  25                  30 ttc ctc aag tgg ctg gac atc tac tgc ccc cac gtc ccc ttc att ttc      144
Phe Leu Lys Trp Leu Asp Ile Tyr Cys Pro His Val Pro Phe Ile Phe
        35                  40                  45 aaa ggc gac gat gac gtc ttc gtc aac ccc acc aac ctg cta gaa ttt      192
Lys Gly Asp Asp Asp Val Phe Val Asn Pro Thr Asn Leu Leu Glu Phe
    50                  55                  60 ctg gct gac cgg cag cca cag gaa aac ctg ttc gtg ggc gat gtc ctg      240
Leu Ala Asp Arg Gln Pro Gln Glu Asn Leu Phe Val Gly Asp Val Leu
65                  70                  75                  80 cag cac gct cgg ccc att cgc agg aaa gac aac aaa tac tac atc ccg      288
Gln His Ala Arg Pro Ile Arg Arg Lys Asp Asn Lys Tyr Tyr Ile Pro
                85                  90                  95 ggg gcc ctg tac ggc aag gcc agc tat ccg ccg tat gca ggc ggc ggt      336
Gly Ala Leu Tyr Gly Lys Ala Ser Tyr Pro Pro Tyr Ala Gly Gly Gly
            100                 105                 110 ggc ttc ctc atg gcc ggc agc ctg gcc cgg cgc ctg cac cat gcc tgc      384
Gly Phe Leu Met Ala Gly Ser Leu Ala Arg Arg Leu His His Ala Cys
        115                 120                 125 gac acc ctg gag ctc tac ccg atc gac gac gtc ttt ctg ggc atg tgc      432
Asp Thr Leu Glu Leu Tyr Pro Ile Asp Asp Val Phe Leu Gly Met Cys
    130                 135                 140 ctg gag gtg ctg ggc gtg cag ccc acg gcc cac gag ggc ttc aag act      480
Leu Glu Val Leu Gly Val Gln Pro Thr Ala His Glu Gly Phe Lys Thr
145                 150                 155                 160 ttc ggc atc tcc cgg aac cgc aac agc cgc atg aac aag gag ccg tgc      528
Phe Gly Ile Ser Arg Asn Arg Asn Ser Arg Met Asn Lys Glu Pro Cys
                165                 170                 175 ttt ttc cgc gcc atg ctc gtg gtg cac aag ctg ctg ccc cct gag ctg      576
Phe Phe Arg Ala Met Leu Val Val His Lys Leu Leu Pro Pro Glu Leu
            180                 185                 190
```

```
ctc gcc atg tgg ggg ctg gtg cac agc aat ctc acc tgc tcc cgc aag       624
Leu Ala Met Trp Gly Leu Val His Ser Asn Leu Thr Cys Ser Arg Lys
        195                 200                 205 ctc cag gtg ctc tgaccccagc cgggctacta ggacaggcca gggcacttgc           676
Leu Gln Val Leu
    210 tcctgagccc ccatggtatt ggggctggag ccacagtgcc caggcctagc ctttggtccc     736 caaggggagg tggagggttg aggcctacgt gccactgggt gtggtggggt gcaggtagcc     796 agaaagggac ctccctgtgt ggataattct aggaaactga ggcccaggaa cg             848

<210> SEQ ID NO 8
<211> LENGTH: 987
<212> TYPE: DNA
<213> ORGANISM: Homo sapiens

<400> SEQUENCE: 8 atg gcc tct cag ggg ccc cag gcc tgg gac gtg acc acc act aac tgc       48
Met Ala Ser Gln Gly Pro Gln Ala Trp Asp Val Thr Thr Thr Asn Cys
 1               5                  10                  15 tca gcc aat atc aac ttg acc cac cag ccc tgg ttc cag gtc ctg gag       96
Ser Ala Asn Ile Asn Leu Thr His Gln Pro Trp Phe Gln Val Leu Glu
                20                  25                  30 ccg cag ttc cgg cag ttt ctc ttc tac cgc cac tgc cgc tac ttc ccc       144
Pro Gln Phe Arg Gln Phe Leu Phe Tyr Arg His Cys Arg Tyr Phe Pro
            35                  40                  45 atg ctg ctg aac cac ccg gag aag tgc agg ggc gat gtc tac ctg ctg       192
Met Leu Leu Asn His Pro Glu Lys Cys Arg Gly Asp Val Tyr Leu Leu
        50                  55                  60 gtg gtt gtc aag tcg gtc atc acg cag cac gac cgc cgc gag gcc atc       240
Val Val Val Lys Ser Val Ile Thr Gln His Asp Arg Arg Glu Ala Ile
 65              70                  75                  80 cgc cag acc tgg ggc cgc gag cgg cag tcc gcg ggt ggg ggc cga ggc       288
Arg Gln Thr Trp Gly Arg Glu Arg Gln Ser Ala Gly Gly Gly Arg Gly
                85                  90                  95 gcc gtg cgc acc ctc ttc ctg ctg ggc acg gcc tcc aag cag gag gag       336
Ala Val Arg Thr Leu Phe Leu Leu Gly Thr Ala Ser Lys Gln Glu Glu
            100                 105                 110 cgc acg cac tac cag cag ctg ctg gcc tac gaa gac cgc ctc tac ggc       384
Arg Thr His Tyr Gln Gln Leu Leu Ala Tyr Glu Asp Arg Leu Tyr Gly
        115                 120                 125 gac atc ctg cag tgg ggc ttt ctc gac acc ttc ttc aac ctg acc ctc       432
Asp Ile Leu Gln Trp Gly Phe Leu Asp Thr Phe Phe Asn Leu Thr Leu
    130                 135                 140 aag gag atc cac ttc ctc aag tgg ctg gac atc tac tgc ccc cac gtc       480
Lys Glu Ile His Phe Leu Lys Trp Leu Asp Ile Tyr Cys Pro His Val
145                 150                 155                 160 ccc ttc att ttc aaa ggc gac gat gac gtc ttc gtc aac ccc acc aac       528
Pro Phe Ile Phe Lys Gly Asp Asp Asp Val Phe Val Asn Pro Thr Asn
                165                 170                 175 ctg cta gaa ttt ctg gct gac cgg cag cca cag gaa aac ctg ttc gtg       576
Leu Leu Glu Phe Leu Ala Asp Arg Gln Pro Gln Glu Asn Leu Phe Val
            180                 185                 190 ggc gat gtc ctg cag cac gct cgg ccc att cgc agg aaa gac aac aaa       624
Gly Asp Val Leu Gln His Ala Arg Pro Ile Arg Arg Lys Asp Asn Lys
        195                 200                 205 tac tac atc ccg ggg gcc ctg tac ggc aag gcc agc tat ccg ccg tat       672
Tyr Tyr Ile Pro Gly Ala Leu Tyr Gly Lys Ala Ser Tyr Pro Pro Tyr
    210                 215                 220
```

```
gca ggc ggc ggt ggc ttc ctc atg gcc ggc agc ctg gcc cgg cgc ctg      720
Ala Gly Gly Gly Gly Phe Leu Met Ala Gly Ser Leu Ala Arg Arg Leu
225                 230                 235                 240 cac cat gcc tgc gac acc ctg gag ctc tac ccg atc gac gac gtc ttt      768
His His Ala Cys Asp Thr Leu Glu Leu Tyr Pro Ile Asp Asp Val Phe
                245                 250                 255 ctg ggc atg tgc ctg gag gtg ctg ggc gtg cag ccc acg gcc cac gag      816
Leu Gly Met Cys Leu Glu Val Leu Gly Val Gln Pro Thr Ala His Glu
            260                 265                 270 ggc ttc aag act ttc ggc atc tcc cgg aac cgc aac agc cgc atg aac      864
Gly Phe Lys Thr Phe Gly Ile Ser Arg Asn Arg Asn Ser Arg Met Asn
        275                 280                 285 aag gag ccg tgc ttt ttc cgc gcc atg ctc gtg gtg cac aag ctg ctg      912
Lys Glu Pro Cys Phe Phe Arg Ala Met Leu Val Val His Lys Leu Leu
    290                 295                 300 ccc cct gag ctg ctc gcc atg tgg ggg ctg gtg cac agc aat ctc acc      960
Pro Pro Glu Leu Leu Ala Met Trp Gly Leu Val His Ser Asn Leu Thr
305                 310                 315                 320 tgc tcc cgc aag ctc cag gtg ctc tga                                  987
Cys Ser Arg Lys Leu Gln Val Leu
                325
```

<210> SEQ ID NO 9
<211> LENGTH: 401
<212> TYPE: PRT
<213> ORGANISM: Homo sapiens

<400> SEQUENCE: 9

```
Met Ser Leu Trp Lys Lys Thr Val Tyr Arg Ser Leu Cys Leu Ala Leu
1               5                   10                  15

Ala Leu Leu Val Ala Val Thr Val Phe Gln Arg Ser Leu Thr Pro Gly
            20                  25                  30

Gln Phe Leu Gln Glu Pro Pro Pro Thr Leu Glu Pro Gln Lys Ala
        35                  40                  45

Gln Lys Pro Asn Gly Gln Leu Val Asn Pro Asn Asn Phe Trp Lys Asn
    50                  55                  60

Pro Lys Asp Val Ala Ala Pro Thr Pro Met Ala Ser Gln Gly Pro Gln
65                  70                  75                  80

Ala Trp Asp Val Thr Thr Thr Asn Cys Ser Ala Asn Ile Asn Leu Thr
                85                  90                  95

His Gln Pro Trp Phe Gln Val Leu Glu Pro Gln Phe Arg Gln Phe Leu
            100                 105                 110

Phe Tyr Arg His Cys Arg Tyr Phe Pro Met Leu Leu Asn His Pro Glu
        115                 120                 125

Lys Cys Arg Gly Asp Val Tyr Leu Leu Val Val Val Lys Ser Val Ile
    130                 135                 140

Thr Gln His Asp Arg Arg Glu Ala Ile Arg Gln Thr Trp Gly Arg Glu
145                 150                 155                 160

Arg Gln Ser Ala Gly Gly Arg Gly Ala Val Arg Thr Leu Phe Leu
                165                 170                 175

Leu Gly Thr Ala Ser Lys Gln Glu Glu Arg Thr His Tyr Gln Gln Leu
            180                 185                 190

Leu Ala Tyr Glu Asp Arg Leu Tyr Gly Asp Ile Leu Gln Trp Gly Phe
        195                 200                 205

Leu Asp Thr Phe Phe Asn Leu Thr Leu Lys Glu Ile His Phe Leu Lys
    210                 215                 220
```

-continued

```
Trp Leu Asp Ile Tyr Cys Pro His Val Pro Phe Ile Phe Lys Gly Asp
225                 230                 235                 240

Asp Asp Val Phe Val Asn Pro Thr Asn Leu Leu Glu Phe Leu Ala Asp
            245                 250                 255

Arg Gln Pro Gln Glu Asn Leu Phe Val Gly Asp Val Leu Gln His Ala
        260                 265                 270

Arg Pro Ile Arg Arg Lys Asp Asn Lys Tyr Tyr Ile Pro Gly Ala Leu
    275                 280                 285

Tyr Gly Lys Ala Ser Tyr Pro Pro Tyr Ala Gly Gly Gly Phe Leu
290                 295                 300

Met Ala Gly Ser Leu Ala Arg Arg Leu His His Ala Cys Asp Thr Leu
305                 310                 315                 320

Glu Leu Tyr Pro Ile Asp Asp Val Phe Leu Gly Met Cys Leu Glu Val
                325                 330                 335

Leu Gly Val Gln Pro Thr Ala His Glu Gly Phe Lys Thr Phe Gly Ile
            340                 345                 350

Ser Arg Asn Arg Asn Ser Arg Met Asn Lys Glu Pro Cys Phe Phe Arg
        355                 360                 365

Ala Met Leu Val Val His Lys Leu Leu Pro Pro Glu Leu Leu Ala Met
    370                 375                 380

Trp Gly Leu Val His Ser Asn Leu Thr Cys Ser Arg Lys Leu Gln Val
385                 390                 395                 400

Leu

<210> SEQ ID NO 10
<211> LENGTH: 24
<212> TYPE: DNA
<213> ORGANISM: Artificial Sequence
<220> FEATURE:
<223> OTHER INFORMATION: Oligonucleotide primer for PCR

<400> SEQUENCE: 10
cagcagctgc tggcctacga agac                                          24

<210> SEQ ID NO 11
<211> LENGTH: 24
<212> TYPE: DNA
<213> ORGANISM: Artificial Sequence
<220> FEATURE:
<223> OTHER INFORMATION: Oligonucleotide primer for PCR

<400> SEQUENCE: 11
gcacatgccc agaaagacgt cgtc                                          24

<210> SEQ ID NO 12
<211> LENGTH: 24
<212> TYPE: DNA
<213> ORGANISM: Artificial Sequence
<220> FEATURE:
<223> OTHER INFORMATION: Oligonucleotide primer for PCR

<400> SEQUENCE: 12
cgttcctggg cctcagtttc ctag                                          24

<210> SEQ ID NO 13
<211> LENGTH: 23
<212> TYPE: DNA
<213> ORGANISM: Artificial Sequence
<220> FEATURE:
<223> OTHER INFORMATION: Oligonucleotide primer for PCR
```

```
<400> SEQUENCE: 13
gaccgacttg acaaccacca gca                                          23

<210> SEQ ID NO 14
<211> LENGTH: 23
<212> TYPE: DNA
<213> ORGANISM: Artificial Sequence
<220> FEATURE:
<223> OTHER INFORMATION: Oligonucleotide primer for PCR

<400> SEQUENCE: 14
gtagacatcg cccctgcact tct                                          23

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer for PCR

<400> SEQUENCE: 15
gcccagagct gcgagccgct                                              20

<210> SEQ ID NO 16
<211> LENGTH: 22
<212> TYPE: DNA
<213> ORGANISM: Artificial Sequence
<220> FEATURE:
<223> OTHER INFORMATION: Oligonucleotide primer for PCR

<400> SEQUENCE: 16
gcacatgccc agaaagacgt cg                                           22

<210> SEQ ID NO 17
<211> LENGTH: 53
<212> TYPE: DNA
<213> ORGANISM: Artificial Sequence
<220> FEATURE:
<223> OTHER INFORMATION: Oligonucleotide primer for PCR

<400> SEQUENCE: 17
ggggacaagt ttgtacaaaa aagcaggctt cgcctctcag gggccccagg cct          53

<210> SEQ ID NO 18
<211> LENGTH: 54
<212> TYPE: DNA
<213> ORGANISM: Artificial Sequence
<220> FEATURE:
<223> OTHER INFORMATION: Oligonucleotide primer for PCR

<400> SEQUENCE: 18
ggggaccact ttgtacaaga aagctgggtc catgggggct caggagcaag tgcc         54

<210> SEQ ID NO 19
<211> LENGTH: 94
<212> TYPE: DNA
<213> ORGANISM: Artificial Sequence
<220> FEATURE:
<223> OTHER INFORMATION: template for PCR

<400> SEQUENCE: 19
gatcatgcat tttcaagtgc agattttcag cttcctgcta atcagtgcct cagtcataat   60
gtcacgtgga gattacaagg acgacgatga caag                               94
```

```
<210> SEQ ID NO 20
<211> LENGTH: 26
<212> TYPE: DNA
<213> ORGANISM: Artificial Sequence
<220> FEATURE:
<223> OTHER INFORMATION: Oligonucleotide primer for PCR

<400> SEQUENCE: 20
cgggatccat gcattttcaa gtgcag                                    26

<210> SEQ ID NO 21
<211> LENGTH: 25
<212> TYPE: DNA
<213> ORGANISM: Artificial Sequence
<220> FEATURE:
<223> OTHER INFORMATION: Oligonucleotide primer for PCR

<400> SEQUENCE: 21
ggaattcttg tcatcgtcgt ccttg                                     25

<210> SEQ ID NO 22
<211> LENGTH: 21
<212> TYPE: DNA
<213> ORGANISM: Artificial Sequence
<220> FEATURE:
<223> OTHER INFORMATION: Oligonucleotide primer for PCR

<400> SEQUENCE: 22
ttcctcaagt ggctggacat c                                         21

<210> SEQ ID NO 23
<211> LENGTH: 19
<212> TYPE: DNA
<213> ORGANISM: Artificial Sequence
<220> FEATURE:
<223> OTHER INFORMATION: Oligonucleotide primer for PCR

<400> SEQUENCE: 23
gccggtcagc cagaaattc                                            19

<210> SEQ ID NO 24
<211> LENGTH: 21
<212> TYPE: DNA
<213> ORGANISM: Artificial Sequence
<220> FEATURE:
<223> OTHER INFORMATION: Oligonucleotide probe

<400> SEQUENCE: 24
actgccccca cgtccccttc a                                         21

<210> SEQ ID NO 25
<211> LENGTH: 55
<212> TYPE: DNA
<213> ORGANISM: Artificial Sequence
<220> FEATURE:
<223> OTHER INFORMATION: Oligonucleotide primer for PCR

<400> SEQUENCE: 25
ggggacaagt ttgtacaaaa aagcaggctt ctggcgccca gagctgcgag ccgct    55

<210> SEQ ID NO 26
<211> LENGTH: 54
<212> TYPE: DNA
<213> ORGANISM: Artificial Sequence
<220> FEATURE:
<223> OTHER INFORMATION: Oligonucleotide primer for PCR
```

```
<400> SEQUENCE: 26
ggggaccact ttgtacaaga aagctgggtc catgggggct caggagcaag tgcc        54

<210> SEQ ID NO 27
<211> LENGTH: 22
<212> TYPE: PRT
<213> ORGANISM: Artificial Sequence
<220> FEATURE:
<223> OTHER INFORMATION: Igk signal sequence

<400> SEQUENCE: 27

Met His Phe Gln Val Gln Ile Phe Ser Phe Leu Leu Ile Ser Ala Ser
1               5                   10                  15

Val Ile Met Ser Arg Gly
            20

<210> SEQ ID NO 28
<211> LENGTH: 8
<212> TYPE: PRT
<213> ORGANISM: Artificial Sequence
<220> FEATURE:
<223> OTHER INFORMATION: FLAG peptide sequence

<400> SEQUENCE: 28

Asp Tyr Lys Asp Asp Asp Asp Lys
1               5
```

N-ACETYLGLUCOSAMINE TRANSFERASE, NUCLEIC ACID ENCODING THE SAME AND USE THEREOF IN DIAGNOSING CANCER AND/OR TUMOR

TECHNICAL FIELD

The present invention relates to a novel enzyme having an activity to transfer N-acetylglucosamine to a non-reducing terminal of Galβ1-4Glc or Galβ1-4GlcNAc group through β1,3-linkage, and to a nucleic acid coding for the same, as well as to nucleic acids for measuring the nucleic acid. The present invention further relates to diagnosis of cancer or tumor using the expression amount of the above-mentioned enzyme or the gene thereof as an index.

BACKGROUND ART

Five types of enzymes are known, having an activity to transfer N-acetylglucosamine to a non-reducing terminal of Galβ1-4Glc or Galβ1-4GlcNAc group through β1,3-linkage, which activity is involved in the synthesis of polylactosamine sugar chains (Togayachi, A. et al., J Biol Chem, 2001, 276, 22032–40; Shiraishi, N. et al., J Biol Chem, 2001, 276, 3498–507; Sasaki, K et al., Proc Natl Acad Sci USA, 1997, 94, 14294–9). However, although the amount of polylactosamine on cell surfaces is increased by making the cells express the gene of the enzyme, some of the enzymes expressed have very low activities. Thus, although it is thought that the enzymes which produce polylactosamine have different characteristics, the characterization of the enzymes has not been sufficient. Therefore, to prepare or produce the polylactosamine sugar chain structure which requires the enzyme activity, it is necessary to chemically synthesize the structure, isolating the structure from a biological component or to synthesize the structure enzymatically using a tissue homogenate.

It is known that sugar chain structures such as Lewis antigen exist on the sugar chain structures based on polylactosamine sugar chains (Kannagi R. Glycoconj J. 1997 August; 14(5):577–84. Review; Nishihara S et al., J Biol. Chem. 1994 Nov. 18; 269(46):29271–8). Similarly, it is said that the structures such as the lengths of polylactosamine sugar chains are involved in cellular immunity by NK cells or the like (Ohyama C et a., EMBO J. 1999 Mar. 15; 18(6):1516–25). Similarly, it is known that human stomach tissue is infected with *Helicobacter pylori* through a related sugar chain such as Lewis antigen (Wang G et al., Mol Microbiol. 2000 June; 36(6):1187–96. Review; Falk PG et al., Proc Natl Acad Sci USA. 1995 Feb. 28; 92(5):1515–9). Thus, if the gene of an enzyme having an activity to transfer N-acetylglucosamine to a non-reducing terminal of Galβ1-4Glc or Galβ1-4GlcNAc group through β1,3-linkage can be cloned, and if the enzyme can be produced by a genetic engineering process using the gene, an antibody to the enzyme may also be produced. Therefore, these are useful for the diagnoses, therapies and prophylactics of cancers, immune diseases and infectious diseases by *pylori*. However, the enzyme has not yet been purified or isolated, and there is no clue to the isolation of the enzyme and identification of the gene. As a result, an antibody to the enzyme has not been prepared.

DISCLOSURE OF THE INVENTION

Accordingly, an object of the present invention is to provide an enzyme having an activity to transfer N-acetylglucosamine to a non-reducing terminal of Galβ1-4Glc or Galβ1-4GlcNAc group through β1,3-linkage, and a nucleic acid coding for the same. Another object of the present invention is to provide a recombinant vector which expresses the above-mentioned nucleic acid in a host cell, to provide a cell in which the nucleic acid is introduced and which expresses the nucleic acid and the enzyme protein, and to provide the enzyme protein. Still another object of the present invention is to provide a nucleic acid for measurement of the above-mentioned nucleic acid according to the present invention, and to provide a method for producing the enzyme having the activity.

As mentioned above, since the enzyme of interest has not been isolated, it is impossible to know its partial amino acid sequence. In general, it is not easy to isolate and purify a protein contained in cells in a trace amount, and so isolation of the enzyme from cells, which has not been isolated so far, is expected not easy. The present inventors thought that if there is a homologous region among the nucleotide sequences of the various enzyme genes, which enzymes have relatively similar actions to that of the enzyme of interest, the gene of the enzyme of interest may also have the homologous sequence. After searching the nucleotide sequences of the known β1,3-N-acetylglucosaminyltransferase genes, β1,3-galactoslytransferase genes and β1,3-N-acetylgalactosaminyltransferase genes, a homologous region was discovered. Thus, based on the cloning by PCR using cDNA library, in which a primer was set in the homologous region, and after various considerations, the present inventors succeeded in the cloning of the gene of the enzyme, and its nucleotide sequence and the deduced amino acid sequence were determined, thereby accomplishing the present invention.

That is, the present invention provides a protein having the amino acid sequence shown in SEQ ID NO: 1 in SEQUENCE LISTING, or a protein having the same amino acid sequence as shown in SEQ ID NO:1 except that one or more amino acids are substituted or deleted, or that one or more amino acids are inserted or added, which has an activity to transfer N-acetylglucosamine to a non-reducing terminal of Galβ1-4Glc or Galβ1-4GlcNAc group through β1,3-linkage. The present invention also provides a nucleic acid coding for the protein. The present invention further provides a recombinant vector containing the nucleic acid, which can express the nucleic acid in a host cell. The present invention still further provides a cell which is transformed by the recombinant vector, which expresses the nucleic acid. The present invention still further provides a nucleic acid for measurement of the nucleic acid, which specifically hybridizes with the nucleic acid. The present invention still further provides use of the nucleic acid for measurement for the diagnosis of a cancer or tumor. The present invention still further provides a method for diagnosis of a cancer or tumor, comprising determining the amount of the above-mentioned enzyme or determining the expression amount of the gene coding for the enzyme, in (a) sample cell(s) separated from body. The present invention still further provides a method for measuring the above-mentioned nucleic acid according to the present invention, comprising annealing the nucleic acid for measurement of nucleic acid, according to the present invention, and the above-described nucleic acid according to the present invention so as to hybridize them, and measuring the hybridized nucleic acid. The present invention still further provides use of the nucleic acid for measurement of nucleic acid, according to the present invention, for the production of nucleic acid for measurement of nucleic acid according to the present invention. The present invention still further provides use of the nucleic acid for measurement of nucleic acid, according to the present invention, for the production of diagnostic reagent for a cancer and/or tumor.

By the present invention, an enzyme having an activity to transfer N-acetylglucosamine to a non-reducing terminal of Galβ1-4Glc or Galβ1-4GlcNAc group through β1,3-linkage, and a nucleic acid encoding the enzyme were first provided. Further, by the present invention, a nucleic acid for measuring the above-mentioned nucleic acid was first provided. Still further, a simple and accurate method for diagnosis of a cancer or tumor, especially a cancer or tumor of digestive organs, and a nucleic acid for measurement used therefor were first provided. Thus, it is expected that the present invention will greatly contribute to the diagnoses of cancers and tumors of digestive organs.

BEST MODE FOR CARRYING OUT THE INVENTION

Figure 1:
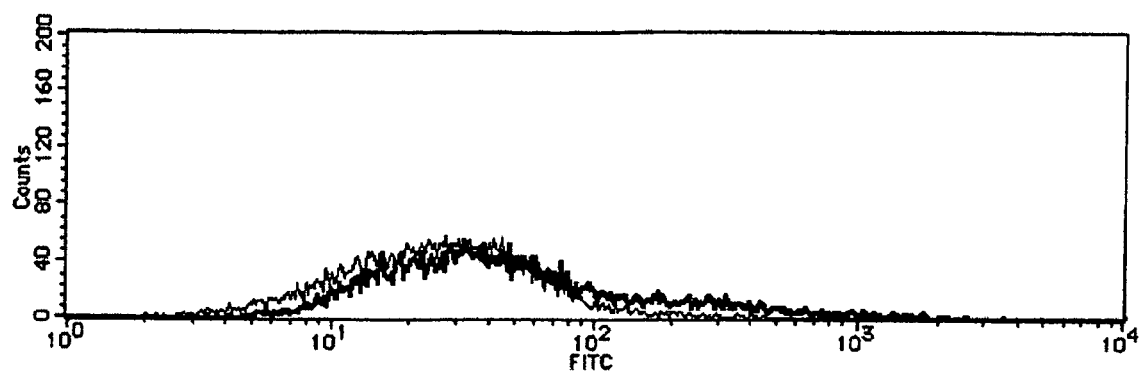
FIG. 1 shows the results of the flow cytometry showing the binding property between the HCT15 colon cancer cell line and the LEA lectin, the cell line being transformed with a recombinant vector into which the gene of the present invention was incorporated or with a recombinant vector into which the gene of the present invention was not incorporated.

The nucleic acid resulting from the removal of the initiation codon (ATG) from the nucleic acid encoding the protein of the present invention, which was cloned from a human antrum cDNA library by the method that will be described in detail in the Examples below, has the nucleotide sequence shown in SEQ ID NO: 4 in the SEQUENCE LISTING, and the deduced amino acid sequence encoded thereby is described below the nucleotide sequence. In SEQ ID NO:3, the amino acid sequence alone is shown. In the Examples below, the nucleic acid having the nucleotide sequence shown in SEQ ID NO:4 was incorporated into an expression vector, expressed in insect cells and it was confirmed that a protein having the above-mentioned enzyme activity was produced. By comparing the amino acid sequence shown in SEQ ID NO:3 and the amino acid sequence of a similar enzyme (concrete enzyme name: β3GnT2: AB049584 which is the gene of β-1,3-N-acetylglucosaminyltransferase), it is thought that the region with a relatively high homology, that is, the region from the 45th amino acid to the C-terminal of the amino acid sequence shown in SEQ ID NO:3 is the active domain of the enzyme, and that the above-mentioned enzyme activity is exhibited if this region consisting of 283 amino acids is contained. This 283 amino acids is shown in SEQ ID NO:1 and the nucleic acid encoding this, taken out from SEQ ID NO:4, is shown in SEQ ID NO:2.

The protein (named "β3GnT-7") according to the present invention obtained in the Examples below is an enzyme having the following characteristics. Each of the characteristics as well as the methods for measuring them are described in detail in the Examples below.

Action: Transfer N-acetylglucosamine to a non-reducing terminal of Galβ1-4Glc group or Galβ1-4GlcNAc group through β1,3-linkage. The reaction catalyzed by the enzyme, expressed in terms of reaction equation, is as follows: UDP-N-acetyl-D-glucosamine+β-D-galactosyl-1,4-D-glucosyl-R→UDP+N-acetyl-β-D-glucosaminyl-1, 3-β-D-galactosyl-1,4-D-glucosyl-R, or UDP-N-acetyl-D-glucosamine+β-D-galactosyl-1,4-N-acetyl-D-glucosaminyl-R→UDP+N-acetyl-β-D-glucosaminyl-1,3-β-D-galactosyl-1,4-N-acetyl-D-glucosaminyl-R Substrate Specificity: Galβ1-4Glc group or Galβ1-4GlcNAc group. In biological substances, these groups occurs abundantly as, for example, polylactosamine structures in glycoproteins (O-glycans and N-glycans) and glycolipids (lacto•neolacto series sugar chains and the like). Further, the Galβ1-4Glc groups or Galβ1-4GlcNAc groups contained in the basal structures of proteoglycans (keratan sulfate) and the like.

In general, it is well-known in the art that there are cases wherein the physiological activity of a physiologically active protein such as an enzyme is retained even if the amino acid sequence of the protein is modified such that one or more amino acids in the amino acid sequence is substituted or deleted, or one or more amino acids are inserted or added to the amino acid sequence. Therefore, a protein having the same amino acid sequence as shown in SEQ ID NO:1 or 3 except that one or more amino acids are substituted or deleted, or one or more amino acids are inserted or added, which protein has an activity to transfer N-acetylglucosamine to a non-reducing group of Galβ1-4Glc or Galβ1-4GlcNAc group through β1,3-linkage (the protein is hereinafter referred to as "modified protein" for convenience) is also within the scope of the present invention. The amino acid sequence of such a modified protein preferably has a homology of not less than 70%, preferably not less than 90%, still more preferably not less than 95% to the amino acid sequence shown in SEQ ID NO: 1 or 3. The homology of the nucleotide sequence may easily be calculated by using a well-known software such as FASTA, and such a software is available on the internet. Further, as the modified protein, one having the same amino acid sequence as shown in SEQ ID NO:1 or 3 except that one or several amino acids are substituted or deleted, or that one or several amino acids are inserted or added is especially preferred. Further, a protein containing the protein having the amino acid sequence shown in SEQ ID NO:1 or 3, or a modified protein thereof, which has an activity to transfer N-acetylglucosamine to a non-reducing terminal of Galβ1-4Glc or Galβ1-4GlcNAc group through β1,3-linkage is also within the scope of the present invention. For example, in the Examples below, a nucleic acid encoding a membrane-bound type enzyme, in which a transmembrane region is ligated to the upstream of the amino acid sequence shown in SEQ ID NO:3 was also cloned, and such a membrane-bound type enzyme is also within the scope of the present invention.

The present invention also provides nucleic acids coding for the amino acid sequence shown in SEQ ID NO:1 or 3 and nucleic acids coding for the amino acid sequences of the above-mentioned modified proteins. As the nucleic acid, DNA is preferred. As is well-known, due to degeneracy, there may be a plurality of codons each of which codes for the same single amino acid. However, as long as a nucleic acid codes for the above-described amino acid sequence, any nucleic acid having any nucleotide sequence is within the scope of the present invention. The nucleotide sequences of the cDNA actually cloned in the Examples below are shown in SEQ ID NOs:2 and 4. Those nucleic acids which hybridize with the nucleic acid having the nucleotide sequence shown in SEQ ID NO:2 or 4 under stringent conditions (i.e., hybridization is performed at 50 to 65° C. using a common hybridization solution such as 5× Denhardt's reagent, 6×SSC, 0.5% SDS or 0.1% SDS), and which code for the above-described modified proteins are within the scope of the present invention.

The above-described nucleic acid according to the present invention can be prepared by the method described in detail in Example below. Alternatively, since the nucleotide sequence was clarified by the present invention, it can easily be prepared by using human antrum as the material and performing the well-known RT-PCR method. The above-described protein according to the present invention can also be easily prepared by, for example, incorporating the above-described nucleic acid according to the present invention into an expression vector, expressing the nucleic acid in a host cell, and purifying the produced protein.

By inserting the above-described nucleic acid according to the present invention into a cloning site of an expression vector, a recombinant vector which can express the above-described nucleic acid in a host cell may be obtained. As the expression vector, various plasmid vectors and virus vectors for various host cells are well-known and commercially available. In the present invention, such a commercially available expression vector may preferably be employed. The methods for transforming or transducing host cells with such a recombinant vector are also well-known. The present invention also provides a cell into which the nucleic acid according to the present invention is introduced by transformation, transduction or transfection, which expresses the nucleic acid. The methods per se for introducing a foreign gene into a host cell are well-known, and the introduction of the foreign gene may easily be attained by, for example, using the above-mentioned recombinant vector. An example of the construction of a recombinant vector and a method for introducing the nucleic acid according to the present invention into host cells using the recombinant vector are described in detail in the Examples below.

Sugar chains may be bound to the protein according to the present invention, as long as the protein has the amino acid sequence described above and has the above-described enzyme activity. In other words, the term "protein" used herein also includes "glycoprotein".

Since the nucleotide sequence of the cDNA of the novel enzyme according to the present invention was clarified by the present invention, nucleic acids for measurement according to the present invention (hereinafter referred to as simply "nucleic acid for measurement"), which specifically hybridize with the mRNA or the cDNA of the enzyme, were provided by the present invention. The term "specifically" herein means that the nucleic acid does not hybridize with other nucleic acids existing in the cells subjected to the test and hybridizes only with the above-described nucleic acid according to the present invention. Although it is preferred, in general, that the nucleic acid for measurement has a sequence homologous with a part of the nucleic acid having the nucleotide sequence shown in SEQ ID NO:2 or 4, mismatch of about 1 or 2 bases does not matter in many cases. The nucleic acid for measurement may be used as a probe or a primer in a nucleic acid-amplification method. To assure specificity, the number of bases in the nucleic acid for measurement is preferably not less than 15, more preferably not less than 18. In cases where the nucleic acid is used as a probe, the size is preferably not less than 15 bases, more preferably not less than 20 bases, and not more than the full length of the coding region. In cases where the nucleic acid is used as a primer, the size is preferably not less than 15 bases, more preferably not less than 18 bases, and less than 50 bases. The methods for measuring a test nucleic acid using a nucleic acid having a sequence complementary to a part of the test nucleic acid as a primer of a gene-amplification method such as PCR or as a probe are well-known, and the methods by which the mRNA of the enzyme according to the present invention was measured by Northern blot or in situ hybridization are concretely described in detail in the Examples below. In the present specification, "measurement" includes detection, quantification and semi-quantification.

The nucleic acid-amplification methods such as PCR are well-known in the art, and reagent kits and apparatuses therefor are commercially available, so that they may easily be carried out. That is, for example, a test nucleic acid serving as a template (e.g., the cDNA of the gene of the enzyme of the present invention) and a pair of nucleic acids for measurement (primers) according to the present invention are mixed in a buffer in the presence of Taq polymerase and dNTPs, and the steps of denaturation, annealing and extension are carried out by changing the temperature of the reaction mixture. Usually, the denaturation step is carried out at 90 to 95° C., the annealing step is carried out at Tm between the template and the primers or a vicinity thereof (preferably within ±4° C.), and the extension step is carried out at 72° C. which is the optimum temperature of Taq polymerase. The reaction time of each step is selected from about 30 seconds to 2 minutes. By repeating this thermal cycle for about 25 to 40 times, the region between the pair of primers is amplified. The nucleic acid-amplification method is not restricted to PCR, but other nucleic acid-amplification methods well-known in the art may also be employed. By carrying out the nucleic acid-amplification method using a pair of the above-described nucleic acids for measurement according to the present invention as primers and using the test nucleic acid as a template, the test nucleic acid is amplified. In contrast, in cases where the test nucleic acid is not contained in the sample, the amplification does not occur. Therefore, by detecting the amplification product, whether the test nucleic acid exists in the sample or not may be determined. Detection of the amplification product may be carried out by a method in which the reaction solution after the amplification is subjected to electrophoresis, and the bands are stained with ethidium bromide or the like, or by a method in which the amplification product after electrophoresis is immobilized on a solid phase such as a nylon membrane, a labeled probe which specifically hybridizes with the test nucleic acid is hybridized with the test nucleic acid, and the label after washing is detected. Alternatively, the test nucleic acid in the sample may be quantified by the so called realtime detection PCR using a quencher fluorescent pigment and a reporter fluorescent pigment. Since the kits for realtime detection PCR are also commercially available, realtime detection PCR may also be carried out easily.

The test nucleic acid may also be semi-quantified based on the intensity of the band resulted in electrophoresis. The test nucleic acid may be a mRNA or a cDNA reverse-transcribed from a mRNA. In cases where a mRNA is amplified as the test nucleic acid, NASBA method (3SR method, TMA method) using the above-described pair of primers may also be employed. NASBA method per se is well-known, and kits therefor are commercially available, so that NASBA method may easily be carried out using the above-described pair of primers.

As the probe, labeled probe obtained by labeling the above-described nucleic acid for measurement with a fluorescent label, radioactive label, biotin label or the like may be used. The methods per se for labeling a nucleic acid are well-known. Whether the test nucleic acid exists in the sample or not may be determined by immobilizing the test nucleic acid or amplification product thereof, hybridizing the labeled probe therewith, and measuring the label bound to the solid phase after washing. Alternatively, the nucleic acid for measurement is immobilized, the test nucleic acid is hybridized therewith, and the test nucleic acid bound to the solid phase is detected by a labeled probe or the like. In such a case, the nucleic acid for measurement immobilized on the solid phase is also called a probe. The methods for measuring a test nucleic acid using a nucleic acid probe are also well-known in the art, and may be attained by making contact between the nucleic acid probe and the test sample in a buffer at Tm or a vicinity thereof (preferably within ±4° C.) so as to hybridize them, and then measuring the hybridized labeled probe or the test nucleic acid bound to the immobilized probe. Such a method includes well-known methods such as Northern blot and in situ hybridization described in the Examples below, as well as Southern blot.

By making the enzyme according to the present invention act on a glycoprotein, oligosaccharide or polysaccharide having (a) Galβ1-4Glc or Galβ1-4GlcNAc group(s), N-acetylglucosamine is bound to the non-reducing terminal(s) of the Galβ1-4Glc or Galβ1-4GlcNAc group(s) through β1,3-linkage. Thus, the enzyme according to the present invention may be used for modification of sugar chains of glycoproteins and for synthesis of saccharides. Further, by administering this enzyme as an immunogen to an animal, an antibody to this enzyme may be prepared, so that the enzyme may be measured by an immunoassay using the antibody. Therefore, the enzyme according to the present invention and the nucleic acid coding for the enzyme are useful for the preparation of such an immunogen. Such an antibody and the above-described nucleic acid for measurement are useful for the measurement of the enzyme in the body, and the measurement is useful for the diagnoses, therapies and preventions of cancers, immune diseases and infectious diseases by *pylori*.

The antibody, preferably the monoclonal antibody, which reacts with the enzyme of the present invention by antigen-antibody reaction, may be prepared by a well-known method comprising administering the enzyme of the present invention as an immunogen to an animal. Such an antibody may be used for the diagnoses of cancers or tumors, preferably cancers or tumors of digestive organs, especially cancer or tumor of colon, more preferably, for the diagnosis of colon cancer. In cases where the antibody is used for the diagnosis of a cancer or tumor, the above-described enzyme is measured by an immunoassay utilizing the antigen-antibody reaction between the enzyme in the sample cells and the antibody, and the result is compared with the measurement results obtained for normal cells. If the measured amount of the enzyme is smaller than that in the normal cells, especially if the enzyme is not detected, it is judged that the possibility that the sample is a cancer or tumor is high. The immunoassays per se are well-known, and any of the well-known immunoassays may be employed. That is, classifying the known immunoassays according to the reaction type, known immunoassays include sandwich immunoassays, competition immunoassays, agglutination immunoassays, Western blot and the like. Classifying the known immunoassays according to the label employed, known immunoassays include fluorescence immunoassays, enzyme immunoassays, radio immunoassays, biotin immunoassays and the like. Any of these immunoassays may be employed. Further, diagnosis may be attained by immunohistostaining. In cases where a labeled antibody is used in the immunoassay, the methods per se for labeling an antibody are well-known, and any of the well-known methods may be employed. It is known that by decomposing an antibody with papain or pepsin, an antibody fragment such as Fab fragment or F(ab')$_2$ fragment having the binding ability with the corresponding antigen (such a fragment is called "antigen-binding fragment" in the present specification) is obtained. The antigen-binding fragments of the antibody of the present invention may also be used in the same manner as the antibody.

These immunoassays per se are well-known in the art, and so it is not necessary to explain these immunoassays in the present specification. Briefly, in sandwich immunoassays, for example, the antibody of the present invention or an antigen-binding fragment thereof is immobilized on a solid phase as a first antibody. The first antibody is then reacted with a sample, and after washing the solid phase, the resultant is then reacted with a second antibody which reacts with the enzyme of the present invention by antigen-antibody reaction. After washing the solid phase, the second antibody bound to the solid phase is measured. By labeling the second antibody with an enzyme, fluorescent substance, radioactive substance, biotin or the like, measurement of the second antibody bound to the solid phase may be attained by measuring the label. The above-mentioned measurement is conducted for a plurality of standard samples each containing a known concentration of the enzyme, and the relationship between the concentrations of the enzyme in the standard samples and the measured amounts of the label is plotted to prepare a calibration curve. The enzyme in a test sample may be quantified by applying the measured amount to the calibration curve. It should be noted that the above-mentioned first antibody and the above-mentioned second antibody may be exchanged. In agglutination immunoassays, the antibody according to the present invention or an antigen-binding fragment thereof is immobilized on particles such as latex particles, and the particles are reacted with a sample, followed by measurement of the absorbance. The above-mentioned measurement is conducted for a plurality of standard samples each containing a known concentration of the enzyme, and the relationship between the concentrations of the enzyme in the standard samples and the measured absorbance is plotted to prepare a calibration curve. The enzyme in a test sample may be determined by applying the measured absorbance to the calibration curve.

The reagents necessary for each type of immunoassay are also well-known in the art. Except for the antibody used, the immunoassay according to the present invention may be carried out using an ordinary kit for immunoassay. For example, such an immunoassay kit may usually include buffer solution, solid phase, labeled second antibody and the like.

As will be concretely described in the Examples below, it was confirmed that diagnoses of cancers and/or tumors can be attained by using the amount of expression of the enzyme of the present invention as an index. Thus, the present invention also provides a method for diagnosis of a cancer or tumor, comprising determining the amount of expression of the gene coding for the enzyme of the present invention, in (a) sample cell(s) separated from body. As will be concretely described in the Examples below, the tumors which can be detected by the diagnosis method according to the present invention are cancers or tumors for which cancers are strongly suspected. As the sample cells, cells of digestive organs are preferred, and cells from colon are especially preferred. By applying the diagnosis method to these cells, cancers or tumors of digestive organs, especially cancer and/or tumor of colon may be diagnosed. The expression amount of the gene may be measured by measuring the amount of the mRNA transcribed from the gene or the amount of the cDNA prepared by using the mRNA as a template, or by measuring the enzyme produced in the sample cells by an immunoassay using the antibody of the present invention. The measurement of the mRNA or cDNA may be carried out using the above-described nucleic acid for measurement according to the present invention by the method described above.

EXAMPLES

The present invention will now be described by way of Examples. However, the present invention is not restricted to the Examples. In the following description, the nucleic acid having the nucleotide sequence shown in SEQ ID NO:5, for example, may also be referred to as "SEQ ID NO:5" for convenience.

1. Search of Gene Database and Determination of Nucleotide Sequence of β3GnT-7

Using analogous genes which are known β1,3-N-acetylglucosaminyltransferase genes, β1,3-galactosyltransferase genes and β1,3-N-acetylgalactosaminyltransferase gene, search of analogous genes was carried out on a gene database. The used sequences were β1,3-N-acetylglucosaminyltransferase genes with accession Nos.: AB049584, AB049585, AB049586 and AB045278; β1,3-galactosyltransferase genes of accession Nos. AF117222, Y15060, Y15014, AB026730, AF145784 and AF145784; and β1,3-N-acetylgalactosaminyltransferase gene with accession No. Y15062 (all of the accession Nos. are of GenBank). The search was carried out using a program tBlastn of BLAST, and all of the amino acid sequences corresponding to ORFs (Open Reading Frames) were included in the search.

As a result, EST sequences with GenBank Accession Nos. AK000770 and a human genomic sequence AC017104 were discovered. Thus, using AC017104, a library was screened.

The used sample was human antrum cDNA library prepared by a conventional method (Yuzuru Ikehara, Hisashi Narimatsu et al, Glycobiology vol. 9 no. 11 pp. 1213–1224, 1999). The screening was carried out by a usual nucleic acid probe method using a radio isotope. The concrete procedures were as follows:

First, using the λ phage prepared from a human antrum cDNA library by a conventional method as templates, PCR was performed using as primers CB-635(5'-cagca gctgc tggcc tacga agac-3') (nt6814–6837 in AC017104) and CB-638 (5'-gcaca tgccc agaaa gacgt cgtc-3') (nt7221–7245). The amplified DNA fragment having a size of about 430 bp was labeled with $^{32}$P-dCTP using Multiple DNA labeling system produced by AMERSHAM.

Using this probe, single plaques which hybridized with this probe were picked up from the plaques of λ phage formed on E. coli. Existence of the target DNA region was confirmed by PCR using the above-mentioned primers CB635 and CB638. Since the phage obtained from the plaques, in which the insertion of the DNA fragment was confirmed was constructed by λ ZAP II vector (STRATAGENE) (Yuzuru Ikehara, Hisashi Narimatsu et al, Glycobiology vol. 9 no. 11 pp. 1213–1224, 1999), a cDNA clone inserted into pBluescript SK vector can be prepared (excision) by the method according to the manufacturer's instruction. The recombinant vector was prepared by this method, and a DNA was obtained from the obtained colony. The cDNA clone was then sequenced (SEQ ID NO:6).

The SEQ ID NO:6 obtained by the above-described method corresponded to nt4828–7052 of AC017104 and lacked the 3' region of ORF. Therefore, the 3' region was cloned after amplification thereof by PCR using the cDNA, and was ligated. That is, a primer CB-625 (5'-cgttc ctggg cctca gtttc ctag-3') (nt7638–7661) corresponding to a region downstream of the termination codon was designed based on the sequence expected from AC017104 resulted from the search by computer, and using this primer in combination with the above-described CB635, a DNA fragment was obtained from the above-described human antrum cDNA library. The obtained DNA fragment was sequenced by a conventional method to obtain SEQ ID NO:7 (nt6814–7661 in AC017104) (hereinafter referred to as "SEQ ID NO:3"). By combining this with SEQ ID NO:6, a theoretical ORF of 978 bp (nt6466–7452 in AC017104) was obtained, and a sequence of 328 amino acids was deduced from this ORF, which was named β3GnT-7 (SEQ ID NO:8). It is known that glycosyltransferases are, in general, type 2 enzymes having one transmembrane segment. However, no hydrophobic region was found in the N-terminal region of this ORF sequence. Since it has been reported that β1,3-N-acetylglucosaminyltransferase activity is detected in human serum (Human Serum Contains N-Acetyllactosamine: β1,3-N-Acetylglucosaminyltransferase Activity. Hosomi, O., Takeya, A., and Kogure, T. J. Biochem. 95, 1655–1659 (1984)), the enzyme encoded by this ORF was a secretory type enzyme having no transmembrane region.

To show that the ORF having the sequence shown in SEQ ID NO:8 and the amino acid sequence encoded thereby actually exist and function (i.e., expressed), existence of the mRNA was checked by RT-PCR and confirmation of the PCR product by a restriction enzyme, and by direct sequencing (usual method) of the PCR product was carried out. As a result, it was confirmed that the above-described theoretical ORF surely existed and actually functioned.

As mentioned above, although it is known that glycosyltransferases are, in general, type 2 enzymes having one transmembrane segment, there is no hydrophobic region in the N-terminal region of the amino acid sequence shown in SEQ ID NO:8, so that the enzyme was thought to be different from the usual glycosyltransferases. Thus, whether a splicing variant having a hydrophobic region (transmembrane segment) in the N-terminal region exists or not was checked by analyzing the nucleotide sequence in the 5' region (i.e., the N-terminal region of the amino acid sequence).

First, using Human stomach Marathon-Ready cDNA (CLONETECH), 5'-RACE (Rapid amplification of cDNA ends) was performed. More particularly, using the AP1 primer included in Marathon cDNA (an adaptor AP1 was attached to the both ends of the DNA fragment, and an adaptor AP2 was attached to the both inner ends thereof) and a primer β3GnT-7RACE-5 (5'-GACCG ACTTG ACAAC CACCA GCA-3') corresponding to the found sequence region, PCR was performed (94° C. for 60 seconds, 5 cycles of 94° C. for 30 seconds–72° C. for 3 minutes, 5 cycles of 94° C. for 30 seconds–70° C. for 3 minutes, and 25 cycles of 94° C.–68° C. for 3 minutes) was performed. The obtained DNA product was subjected to nested PCR (94° C. for 60 seconds, 5 cycles of 94° C. for 30 seconds–72° C. for 3 minutes, 5 cycles of 94° C. for 30 seconds–70° C. for 3 minutes, and 15 cycles of 94° C.–68° C. for 3 minutes) using the AP2 primer included in Marathon cDNA and a primer β3GnT-7RACE-4 (5'-GTAGA CATCG CCCCT GCACT TCT-3'). The obtained product was cloned into pGEMeasy (CLONETECH) and sequenced. As a result, the sequence upstream of the initiation codon of the earlier discovered SEQ ID NO:6 was obtained, and a transmembrane region was observed when deduced into amino acid sequence. However, although the 5' region of the nucleotide sequence in the vicinity of the transmembrane region was analyzed, the initiation codon of the ORF was not found.

Thus, using GeneScan, HMMgene and the like which were softwares for analyzing gene regions, the translation region of the human genomic sequence AC017104 containing β3GnT-7 was analyzed. As a result, a first exon of 11 bases (about 3 amino acid) (nt4331–4341 of AC017104) containing the initiation codon was expected. Thus, using a primer corresponding to an upstream region of the initiation codon, PCR was performed in order to determine whether the expected region existed as a transcript.

More particularly, PCR (30 cycles of 95° C. for 30 seconds, 60° C. for 30 seconds, 72° C. for 60 seconds) was performed using as primers β3GnT-7RACE-8 (5'-GCCCA GAGCT GCGAG CCGCT-3') (nt4278–4300 in AC017104) and CB-638 (5'-GCACA TGCCC AGAAA GACGT CG-3') ((nt7224–7245 in AC017104), as a template Human leukocyte Marathon-Ready cDNA, and LA-Taq (TaKaRa). As a result, an amplification product having a size of 1046 bases was obtained. This PCR product was purified and sequenced. It was proved, as expected from the above-described analysis of the translation region, the 3'-side (nt4341) in the first exon was ligated to nt6258 in a downstream region.

By combining SEQ ID NOs: 6 and 7 and this result, the nucleotide sequence having 1206 bases shown in SEQ ID NO:5 and the amino acid sequence having 401 amino acids shown in SEQ ID NO:9 were obtained. The SEQ ID NO:5 was one in which the upstream regions of 219 bases (73 amino acids) (nt4331–4341 and nt6258–6465 in AC017104) were ligated to SEQ ID NO:8 (combination of SEQ ID NOs:6 and 7), and it was thought that nt4342–6257 was spliced. Since SEQ ID NO:5 contains a transmembrane segment (nt6265–6322 in AC017104), SEQ ID NO:5 and SEQ ID NO:8 were thought to be the transmembrane type and secretory type having the same activity, respectively.

2. Insertion of β3GnT-7 into Expression Vector

To examine the activity of β3GnT-7, β3GnT-7 was expressed in insect cells. Although it is thought that the activity may be confirmed enough by expressing the active region from the 119th amino acid to the C-terminal of SEQ ID NO:9, which region is relatively well conserved in the other genes of the same family, the active region from the 75th amino acid to the C-terminal of β3GnT-7 (SEQ ID NO:9) was expressed.

The gene was incorporated into pFastBac of Gateway system from INVITROGEN, and then a Bacmid by Bac-to-Bac system from INVITROGEN was prepared.

① Preparation of Entry Clone

PCR was performed using β3GnT-7S primer (5'-GGGGA CAAGT TTGTA CAAAA AAGCA GGCTT Cgcct ctcag gggcc ccagg cct-3') and β3GnT-7A primer (5'-GGGGA CCACT TTGTA CAAGA AAGCT GGGTC catgg gggct cagga gcaag tgcc-3') (the nucleotides shown in capital letters were the added sequence attL for GATEWAY hereinbelow described), and as a template the DNA of β3GnT-7 clone (the clone containing the theoretical ORF sequence) generated from the cDNA clone obtained by the screening and the DNA fragment obtained by PCR, to obtain an amplification product.

This product was incorporated into pDONR201 by BP clonase reaction to prepare an "entry clone". The reaction was carried by incubating a mixture of 5 µl of the desired DNA fragment, 1 µl (150 ng) of pDONR201, 2 µl of reaction buffer and 2 µl of BP clonase mix at 25° C. for 1 hour. After adding 1 µl of Proteinase K, the reaction mixture was left to stand at 37° C. for 10 minutes, thereby terminating the reaction.

Then the whole mixture (11 µl) was mixed with 100 µl of competent cells (*E. coli* DH5α), and after heat shock, the mixture was plated on an LB plate containing kanamycin. On the next day, colonies were collected, and existence of the desired DNA was directly confirmed by PCR. For double check, the nucleotide sequence of the DNA was confirmed, and vector (pDONR-β3Gn-T7) was extracted and purified.

② Preparation of Expression Clone

The above-described entry clone has attL at the both ends of the inserted region, the attL being a recombination site used when λ phage is cut out from *E. coli*. By mixing the entry clone with LR clonase (a mixture of recombination enzymes Int, IHF and Xis of λ phage) and a destination vector, the inserted region is transferred to the destination vector so that an expression clone is prepared. These operations will now be described in detail.

Firstly, a mixture of 1 µl of the entry clone, 0.5 µl (75 ng) of pFBIF, 2 µl of LR reaction buffer, 4.5 µl of TE and 2 µl of LR clonase mix were allowed to react at 25° C. for 1 hour, and then 1 µl of Proteinase K was added, followed by incubation at 37° C. for 10 minutes, thereby terminating the reaction (by this recombination reaction, pFBIF-β3Gn-T7 is generated). The pFBIF was one obtained by inserting Igκ signal sequence (MHFQVQIFSFLLISASVIMSRG) and FLAG peptide (DYKDDDDK) for purification. The Igκ signal sequence was inserted in order to change the expressed protein to a secretory protein, and the FLAG peptide was inserted for purification. The DNA fragment obtained by PCR using as a template OT3 (5'-gatca tgcat tttca agtgc agatt ttcag cttcc tgcta atcag tgcct cagtc ataat gtcac gtgga gatta caagg acgac gatga caag-3'), and using primers OT20 (5'-cgggatccat gcattttcaa gtgcag-3') and OT21 (5'-ggaat tcttgt catcg tcgtc cttg-3') was inserted using Bam HI and Eco RI. Further, to insert the Gateway sequence, Conversion cassette was inserted using Gateway Vector Conversion System (INVITROGEN).

Then the whole mixture (11 µl) was mixed with 100 µl of competent cells (*E. coli* DH5α), and after heat shock, the mixture was plated on an LB plate containing ampicillin. On the next day, colonies were collected, and existence of the desired DNA was directly confirmed by PCR, followed by extraction and purification of the vector (pFBIF-p3Gn-T7).

(3) Preparation of Bacmid by Bac-to-Bac System

Using Bac-to-Bac system (INVITROGEN), recombination was carried out between the above-described pFBIF- and pFastBac, and G10 and other sequences were inserted into a Bacmid which was able to replicate in insect cells. With this system, the desired gene is incorporated into the Bacmid by the recombinant protein produced by a helper plasmid, only by incorporating pFastBac into which the desired gene was inserted, using the recombination site of Tn7 into an *E. coli* (DH10BAC) containing the Bacmid. The Bacmid contains lacZ gene, so that classical selection based on the color, that is, blue (no insertion) or white (with insertion), of the colony can be attained.

That is, the above-described purified vector (pFBIH-β3GnT-7) was mixed with 50 μl of competent cells (*E. coli* DH10BAC), and after heat shock, the mixture was plated on an LB plate containing kanamycin, gentamycin, tetracycline, Bluo-gal and IPTG. On the next day, white single colony was further cultured and Bacmid was collected.

3. Introduction of Bacmid into Insect Cells

After confirming that the desired sequence was inserted into the Bacmid obtained from the white colony, the Bacmid was introduced into insect cells Sf21 (commercially available from INVITROGEN). That is, to a 35 mm Petri dish, Sf21 cells in an amount of 9×10$^5$ cells/2 ml (Sf-900SFM (INVITROGEN) containing an antibiotic) were added, and the cells were cultured at 27° C. for 1 hour to adhere the cells. (Solution A): To 5 μl of the purified Bacmid DNA, 100 μl of Sf-900SFM (INVITROGEN) not containing an antibiotic was added. (Solution B): To 6 μl of CellFECTIN Reagent (INVITROGEN), 100 μl of Sf-900SFM (INVITROGEN) not containing an antibiotic was added. Solution A and Solution B were then gently mixed and the mixture was incubated for 15 to 45 minutes at room temperature. After confirming that the cells adhered, the culture medium was aspirated and 2 ml of Sf-900SFM (INVITROGEN) not containing an antibiotic was added. To a solution (lipid-DNA complexes) prepared by mixing Solution A and Solution B, 800 μl of Sf900II not containing an antibiotic was added and the resultant was gently mixed. The culture medium was aspirated, and diluted lipid-DNA complexes solution was added to the cells, followed by incubating the cells at 27° C. for 5 hours. Thereafter, transfection mixture was removed and 2 ml of culture medium Sf-900SFM (INVITROGEN) containing an antibiotic was added, followed by incubating the resultant at 27° C. for 72 hours. Seventy two hours after the transfection, the cells were peeled off by pipetting, and the cells and the culture medium were collected. The cells and the culture medium were centrifuged at 3000 rpm for 10 minutes, and the obtained supernatant was stored in a separate tube (this supernatant is the primary virus solution).

To a T75 culture flask, Sf21 cells in an amount of 1×10$^7$ cells/20 ml of Sf-900SFM (INVITROGEN) (containing an antibiotic) were placed, and the resultant was incubated at 27° C. for 1 hour. After the cells adhered, 800 μl of the primary virus was added and the resultant was cultured at 27° C. for 48 hours. Forty eight hours later, the cells were peeled off by pipetting and the cells and the culture medium were collected. The cells and the culture medium were centrifuged at 3000 rpm for 10 minutes, and the obtained supernatant was stored in a separate tube (this supernatant was used as the secondary virus solution).

Further, to a T75 culture flask, Sf21 cells in an amount of 1×10$^7$ cells/20 ml of Sf-900SFM (INVITROGEN) (containing an antibiotic) were placed, and the resultant was incubated at 27° C. for 1 hour. After the cells adhered, 1000 μl of the secondary virus solution was added and the resultant was cultured at 27° C. for 72 to 96 hours. After the culturing, the cells were peeled off by pipetting and the cells and the culture medium were collected. The cells and the culture medium were centrifuged at 3000 rpm for 10 minutes, and the obtained supernatant was stored in a separate tube (this supernatant was used as the tertiary virus solution). Further, to a 100 ml spinner flask, 100 ml of Sf21 cells at a population of 6×10$^5$ cells/ml was placed, and 1 ml of the tertiary virus solution was added, followed by culturing the cells at 27° C. for about 96 hours. After the culturing, the cells and the culture medium were collected. The cells and the culture medium were centrifuged at 3000 rpm for 10 minutes, and the obtained supernatant was stored in a separate tube (this supernatant was used as the quaternary virus solution).

The primary to tertiary cell pellets were sonicated (sonication buffer: 20 mM HEPES pH7.5, 2% Triton X-100 (trademark)) and the crude cell extract was 20-fold diluted with H$_2$O. The resultant was subjected to SDS-PAGE and then to Western blotting using anti-FLAG M2-peroxidase (A-8592, SIGMA) in order to confirm the expression of β3Gn-T7 protein. As a result, a plurality of broad bands (thought to be due to differences in post-translational modifications by sugar chains or the like) centering at the position of about 38–40 kDa were detected, so that the expression was confirmed.

4. Resin Purification of β3Gn-T7

To 10 ml of the supernatant of FLAG-β3Gn-T7 of the quaternary infection, NaN$_3$ (0.05%), NaCl (150 mM), CaCl$_2$ (2 mM), and anti-M1 resin (SIGMA) (50 μl) were added and the resulting mixture was stirred overnight at 4° C. On the next day, the mixture was centrifuged (3000 rpm for 5 minutes, at 4° C.) and the pellet was collected. To the pellet, 900 μl of 2 mM CaCl2•TBS was added and the resultant was centrifuged again (2000 rpm for 5 minutes, at 4° C.), and the pellet was suspended in 200 μl of 1 mM CaCl2•TBS to obtain a sample (β3GnT-7 enzyme solution) for the measurement of activity.

5. Search of Acceptor Substrate of β3Gn-T7

As a result of molecular evolutionary analysis comparing β3Gn-T7 with β1,3-N-acetylglucosaminyltransferases and β1,3-galactosyltransferases, β3Gn-T7 was classified into β1,3-N-acetylglucosaminyltransferases. Thus, firstly, analysis was performed using UDP-GlcNAc as the donor substrate.

Using the following reaction systems, the acceptor substrate was searched. As the "acceptor substrate" in the reaction solution described below, each of the following was used and whether each of them functioned as the acceptor or not was investigated: pNp-α-Glc, pNp-β-Glc, pNp-α-GlcNAc, pNp-β-GlcNAc, pNp-α-Gal, pNp-β-Gal, pNp-α-GalNAc, Bz-α-GalNAc, pNp-α-Xyl, pNp-β-Xyl, pNp-α-Fuc, Bz-α-Man, Bz-α-ManNAc, LacCer, GalCer type1 and Bz-β-lactoside (all of them are from SIGMA) and Galβ1-4GlcNAc-α-pNp (TRONTO RESEARCH CHEMICAL).

The reaction solution (the numbers in the parentheses indicate the final concentrations) contained acceptor substrate (10 nmol), sodium cacodylate buffer (pH7.2) (50 mM), Triton CF-54 (trademark) (0.4%), MnCl$_2$ (10 mM), UDP-GlcNAC (480 μM) and UDP-[$^{14}$C]GlcNAC (175 nCi) and CDP-colline (5 mM), to which 10 μl of the β3Gn-T7 enzyme solution and H$_2$O were added to attain a final volume of 25 μl.

The reaction mixture was allowed to react at 37° C. for 5 hours, and after completion of the reaction, 200 μl of 0.1 M KCl was added, followed by light centrifugation and collection of the supernatant. The supernatant was passed through Sep-Pak plus C18 Cartridge (WATERS) equilibrated by washing once with 10 ml of methanol and then twice with 10 ml of H$_2$O, so as to adsorb the substrate and the product in the supernatant on the cartridge. After washing the cartridge twice with 10 ml of H$_2$O, the adsorbed substrate and the product were eluted with 5 ml of methanol. The eluted solution was evaporated to dryness by blowing nitrogen gas while heating the solution with a heat block at 40° C. To the resultant, 20 μl of methanol was added, and the resulting mixture was plotted on a TLC plate (HPTLC plate Silica gel 60: MERCK), and developed using a developing solvent having the composition of chloroform:methanol:water (containing 0.2% CaCl$_2$)=65:35:8. After developing the mixture up to 5 mm from the top end of the TLC plate, the plate was dried and the intensity of the radioactivity taken in the product was measured using Bio Image Analyzer FLA3000 (FUJI PHOTO FILM).

As a result, it was proved that β3GnT-7 is a β1,3-N-acetylglucosaminyltrasferase having an activity to transfer GlcNAc to Bz-β-lactoside and Galβ1-4Glc(NAc)-α-pNp, that is, an enzyme which transfers GlcNAc to the galactose at the non-reducing terminal of Galβ1-4Glc(NAc)-R.

6. Measurement of β3GlcNAcT Activity to N-glycan

As the enzyme source, the expressed and purified recombinant enzyme (to which the FLAG sequence is fused) was used as in the case mentioned above. As the acceptor substrates, commercially available PA-bound sugar chain substrates (produced by TAKARA BIO) shown in Table 1 were used. The reaction was carried out in a mixture containing 14 mM sodium cacodylate buffer (pH7.4), 0.4% Triton CF-54, 10 mM MnCl$_2$, 50 mM UDP-GlcNAc (donor substrate), 20 pmol of the acceptor substrate and 100 ng of the enzyme protein solution at 37° C. for 16 hours. The reaction was terminated at 95° C. for 3 minutes, and 80 μl of water was added. The resulting mixture was passed through Ultra-free MC column (WATERS), and 45 μl aliquot of the passed solution was subjected to HPLC. The conditions of the HPLC were as described below. The conversion enzyme activity (%) was determined using a solution which did not contain UDP-GlcNAc (donor substrate) as a control. The results are shown in Table 1 below.

(HPLC Conditions)

Buffer I.a: 100 mM acetic acid/triethylamine, pH 4.0

Buffer I.b: 100 mM acetic acid/triethylamine, pH 4.0 (containing 0.5% 1-butanol)

gradient: 5–55%: Buf. I.b (0–60 min.), flow rate: 1.0 ml/min.

column: PalPak Type R (TaKaRa Cat. No. CA8000)

column oven temp: 40° C.

HPLC System: Shimadzu LC-10AD vp, CTO-10AC vp DGU-14A, cell temp controller

Detector: Fluorescence: RF-10AXL UV: SPD-10Avp

TABLE 1

| Acceptor Substrate | Conversion Activity (%) |
|---|---|
| Galβ1-4GlcNAcβ1-2Manα1\⁶₃Manβ1-4GlcNAcβ1-4GlcNAc-PA / Galβ1-4GlcNAcβ1-2Manα1 | 18.3 |
| Galβ1-4GlcNAcβ1-2Manα1\⁶₃Manβ1-4GlcNAcβ1-4GlcNAc-PA / Galβ1-4GlcNAcβ1⁴₂Manα1 / Galβ1-4GlcNAcβ1 | 26.0 |
| Galβ1-4GlcNAcβ1\⁶₂Manα1 / Galβ1-4GlcNAcβ1 Galβ1-4GlcNAcβ1 \⁶₃Manβ1-4GlcNAcβ1-4GlcNAc-PA / ⁴₂Manα1 / Galβ1-4GlcNAcβ1 | 20.3 |
| Galβ1-4GlcNAcβ1-2Manα1 Fucα1 \⁶₃Manβ1-4GlcNAcβ1-⁶4GlcNAc-PA / Galβ1-4GlcNAcβ1-2Manα1 | 20.6 |
| Galβ1-4GlcNAcβ1-2Manα1 Fucα1 \ Galβ1-4GlcNAcβ1\⁶₃Manβ1-4GlcNAcβ1-⁶4GlcNAc-PA / ⁴₂Manα1 / Galβ1-4GlcNAcβ1 | 17.3 |
| Galβ1-4GlcNAcβ1 \⁶₂Manα1 Fucα1 / \⁶ \⁶ Galβ1-4GlcNAcβ1 Manβ1-4GlcNAcβ1-4GlcNAc-PA Galβ1-4GlcNAcβ1 ₃ / ⁴₂Manα1 / Galβ1-4GlcNAcβ1 | 18.1 |
| Manα1\⁶₃Manβ1-4GlcNAcβ1-4GlcNAc-PA / Manα1 | 0.0 |
| Galβ1-4GlcNAcβ1-3Galβ1-4Glc-PA | — |

7. Measurement of Expression of Enzyme by Flow Cytometry

The β3GnT-7(G10) gene was incorporated into pDEST12.2 vector (INVITROGEN) to prepare pDEST12.2-G10 vector DNA. More particularly, this was carried out as follows: Using primers described below containing the sequence of the Gateway system of INVITROGEN, a cDNA from Colo205 cells (colon cancer cells) was amplified by PCR, and the amplification product was first incorporated into the pDONR vector by BP reaction. After confirming the DNA sequence by sequencing the vector, the insert was transferred from the pDONR vector to pDEST12.2 vector by LR reaction. These operations were carried out using the vectors and reagents contained in the kit of INVITROGEN in accordance with the instructions included in the commercial product.

G10/ORF-F1 Primer
ggggacaagtttgtacaaaaaagcaggcttctggcgcccagagctgcgagccgct (In this, ggggacaagtttgtacaaaaaagcaggcttc is a sequence in the vector)

G10/ORF-R1 Primer
ggggaccactttgtacaagaaagctgggtccatggggctcaggagcaagtgcc (In this, the cDNA sequence of b3GnT7 gene is from catggggctcaggagcaagtgcc) By the above-described procedures, a recombinant vector was obtained in which a DNA fragment containing the cDNA shown in SEQ ID NO:5 to which the region other than the cDNA sequence in the above-described primers was attached to the 5'- and 3'-ends thereof was inserted. This recombinant vector was introduced into HCT15 cell line and LSC cell line (both are colon cancer cell lines) by a conventional method. As a control, the pDEST12.2 vector DNA in which the gene was not incorporated was introduced into the cell lines in the same manner (Mock cells). After carrying out the selection by 0.8 mg/ml of G418 (INVITROGEN) for one month, the cells were harvested. The harvested cells were washed twice with 1% BSA/0.1% NaN3/PBS(−). The cell population was adjusted to 1×10$^7$ cells/ml, and 100 µl (1×10$^6$ cells) aliquot thereof was used for one sample. After centrifugation, the supernatant was removed and the resultant was diluted to a concentration of 10 µg/ml. To the resultant, 100 µl each of the FITC-labeled lectins described below were added, and the cells were suspended. After allowing the reaction at 4° C. in the dark (refrigerator) for 30 minutes, 100 µl of 1% BSA/0.1% NaN$_3$/PBS was added to each well to carry out washing. The resultant was centrifuged at 1000 rpm for 5 minutes, and the supernatant was removed. The washing was repeated once more. The resulting cells were suspended in 1 ml of 0.5% paraformaldehyde/PBS to fix the cells, and analyzed by flow cytometry FACSCalibur (BECTON DICKINSON) after passing the cells through a nylon mesh. The results are shown in FIGS. 1–3.

The used lectins were *Lycopersicon esculentum* (LEA) and *Triticum vulgare* (WGA), both of which recognize the repetition of N-acetyl lactosamine structure, and N-acetyl glucosamine structure, and labeled with FITC (purchased from HONEN, SEIKAGAKU CORPORATION, EY LABORATORIES and so on).

FIG. 1 shows the results of the flow cytometry showing the binding property between the HCT15 colon cancer cell line and the LEA lectin. FIG. 2 shows the results of the flow cytometry showing the binding property between the LSC colon cancer cell line transformed with the recombinant vector containing the gene of the present invention or the vector not containing the gene of the present invention and LEA lectin. FIG. 3 shows the results of the flow cytometry showing the binding property between the HCT15 colon cancer cell line and the WGA lectin. In each of the drawings, the bold line shows the results of the cells transformed with the recombinant vector containing β3GnT-7 gene, and the thin line shows the results of the cells (Mock cells) transformed with the vector not containing β3GnT-7 gene.

Figure 2:
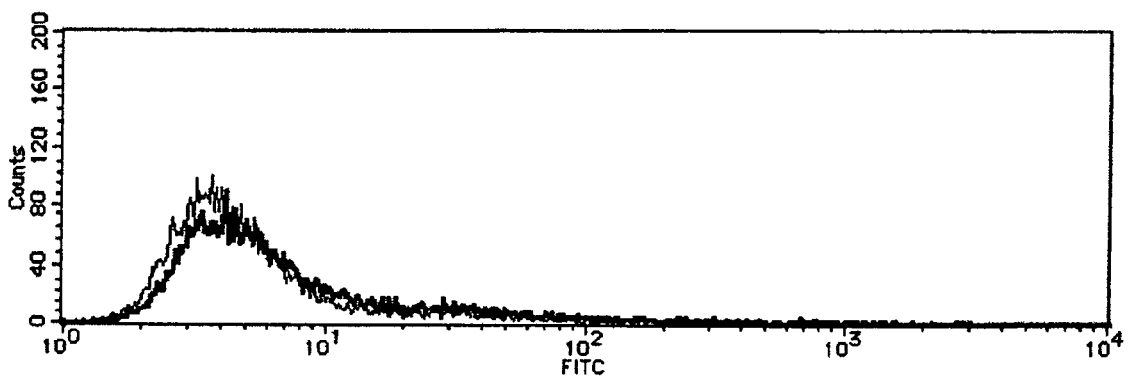
FIG. 2 shows the results of the flow cytometry showing the binding property between the LSC colon cancer cell line and the LEA lectin, the cell line being transformed with a recombinant vector into which the gene of the present invention was incorporated or with a recombinant vector into which the gene of the present invention was not incorporated.
Figure 3:
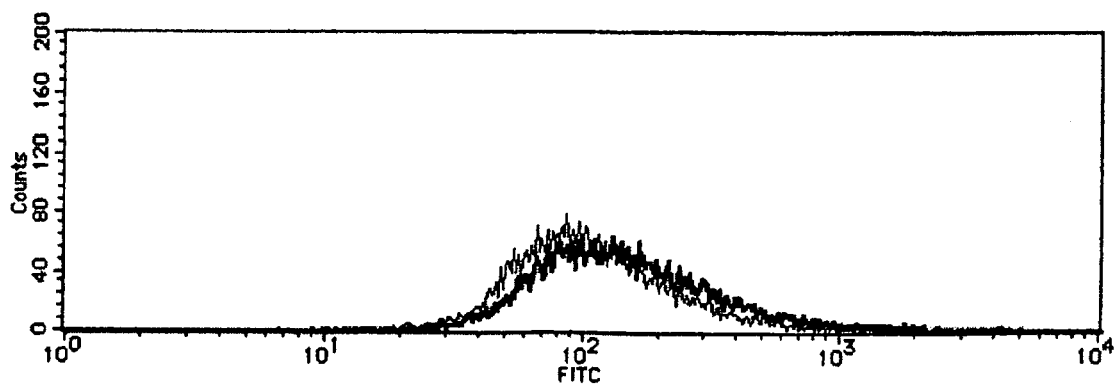
FIG. 3 shows the results of the flow cytometry showing the binding property between the HCT15 colon cancer cell line and the WGA lectin, the cell line being transformed with a recombinant vector into which the gene of the present invention was incorporated or with a recombinant vector into which the gene of the present invention was not incorporated.

As shown in FIGS. 1–3, in all of the cases, the fluorescence intensity was shifted, which indicates that the N-acetyl lactosamine-containing structure was increased in the cells into which the DNA of pDEST12.2-G00 containing β3 GnT-7(G10) gene was incorporated.

8. Analysis of Tissue-specific Expression of β3GnT-7

The expression of the gene in tissues and in cell lines was examined by Real Time PCR method (Gibson, U. E., Heid, C. A., and Williams, P. M. (1996) Genome Res 6, 995–1001). Human tissue cDNAs used as materials were the Marathon cDNAs. From the various cell lines, total RNAs were extracted by a conventional method and the cDNAs were synthesized. For obtaining the calibration curve of β3GnT-7, a plasmid containing β3GnT-7 gene inserted in pDONR™201 vector DNA was used. As a control for the endogenous expression, constantly expressed human glyceraldehyde-3-phosphate dehydrogenase (GAPDH)) was used. For obtaining the calibration curve of GAPDH, a plasmid containing the GAPDH gene in pCR2.1 (INVITROGEN) was used. As the primer set and probe for β3GnT-7, the following were used: RT-β3GnT-7-F2; 5'-TTCCT-CAAGTGGCTGGACATC-3', RT-β3GnT-7-R2;5'-GCCGGTCAGCCAGAAATTC-3', probe; 5'-Fam ACTGCCCCCACGTCCCCTTCA-MGB-3'. As the primer set and probe for GAPDH, a kit (Pre-Developed TaqMan® Assay Reagents Endogenous Human GAPDH (APPLIED BIOSYSTEMS) was used. The PCR was performed using TaqMan Universal PCR Master Mix (APPLIED BIOSYSTEMS) under the conditions of 50° C. for 2 minutes, then at 95° C. for 10 minutes, and repeating 50 cycles of 95° C. for 15 seconds–60° C. for 1 minute. The quantitation of the PCR product was carried out using ABI PRIAM7700 Sequence Detection System (APPLIED BIOSYSTEMS). The expression amount of G11 was normalized by dividing the amount by the amount of the transcription product of the constantly expressed GAPDH. The results for the human tissues are summarized in Table 2, and the results for the cell lines are summarized in Table 3.

TABLE 2

| Tissue | β3GnT-7/GAPDH |
|---|---|
| brain | 0.01045 |
| cerebral cortex | 0.04522 |
| cerebellum | 0.02345 |
| fetal brain | 0.02030 |
| bone marrow | 0.01462 |
| thyroid | 0.04084 |
| thymus | 0.01274 |
| spleen | 0.10108 |
| leukocyte | 0.07876 |
| heart | 0.00956 |
| skeletal muscle | 0.00071 |
| lung | 0.12146 |
| liver | 0.02299 |
| esophagus | 0.00605 |
| stomach | 0.26922 |
| small intestine | 0.09333 |
| colon | 0.07630 |
| pancreas | 0.27317 |
| kidney | 0.01161 |
| adrenal | 0.15069 |
| mammary gland | 0.02560 |
| uterus | 0.07747 |
| placenta | 0.18763 |
| ovary | 0.11465 |
| testis | 0.05323 |

The tissues in which β3GnT-7 was highly expressed were pancreas, stomach, placenta and adrenal, and the tissues in which β3GnT-7 was moderately expressed were colon, leukocyte, lung, ovary, small intestine, spleen, testis, uterus and cerebral cortex. In the tissues other than these tissues, the expression amount was relatively low.

TABLE 3

| Cell (origin) | β3GnT-7/GAPDH |
| --- | --- |
| GOTO (neuroblastoma) | 0.00012 |
| SCCH-26 (neuroblastoma) | 0.00137 |
| T98G (glioblastoma) | 0.00032 |
| U251 (glioblastoma) | 0.00023 |
| Leukemia (premyeloblastic leukemia) | 0.35660 |
| Melanoma (skin) | 0.01255 |
| HL-60 (premyeloblastic leukemia) | 0.17663 |
| K562 (leukemia) | 0.00038 |
| U937 (monocyte) | 0.01617 |
| Daudi (B cell (Burkitt's)) | 0.00437 |
| PC-1 (lung) | 0.00000 |
| EBC-1 (lung) | 0.00121 |
| PC-7 (lung) | 0.00017 |
| HepG2 (liver) | 0.01199 |
| A431 (esophagus) | 0.01031 |
| MKN45 (stomach) | 0.00027 |
| KATOIII (stomach) | 0.03964 |
| HSC43 (stomach) | 0.00031 |
| Colo205 (colon) | 0.00278 |
| HCT15 (colon) | 0.00193 |
| LSC (colon) | 0.00003 |
| LSB (colon) | 0.00128 |
| SW480 (colon) | 0.00045 |
| SW1116 (colon) | 0.13076 |
| Capan-2 (pancreas) | 0.03664 |
| PA-1 (uterus) | 0.00290 |

Expression of β3GnT-7 in cell lines was lower than that in normal tissues. In HL60 cells originated from premyeloblastic leukemia and in SW1116 cells originated from colon, the expression level was high.

It was easily thought that the expression amount of β3GnT-7 is changed when the degree of differentiation is changed by cancerization or the like, so that there is a possibility that measurement of the expression amount of β3GnT-7 may be used for diagnoses of diseases. Further, as described above, there is a possibility that there are two initiation sites in β3GnT-7, so that there is a possibility that by measuring the change of the splicing variants, the state of differentiation and pathological change of the cells may be measured.

Figure 4:
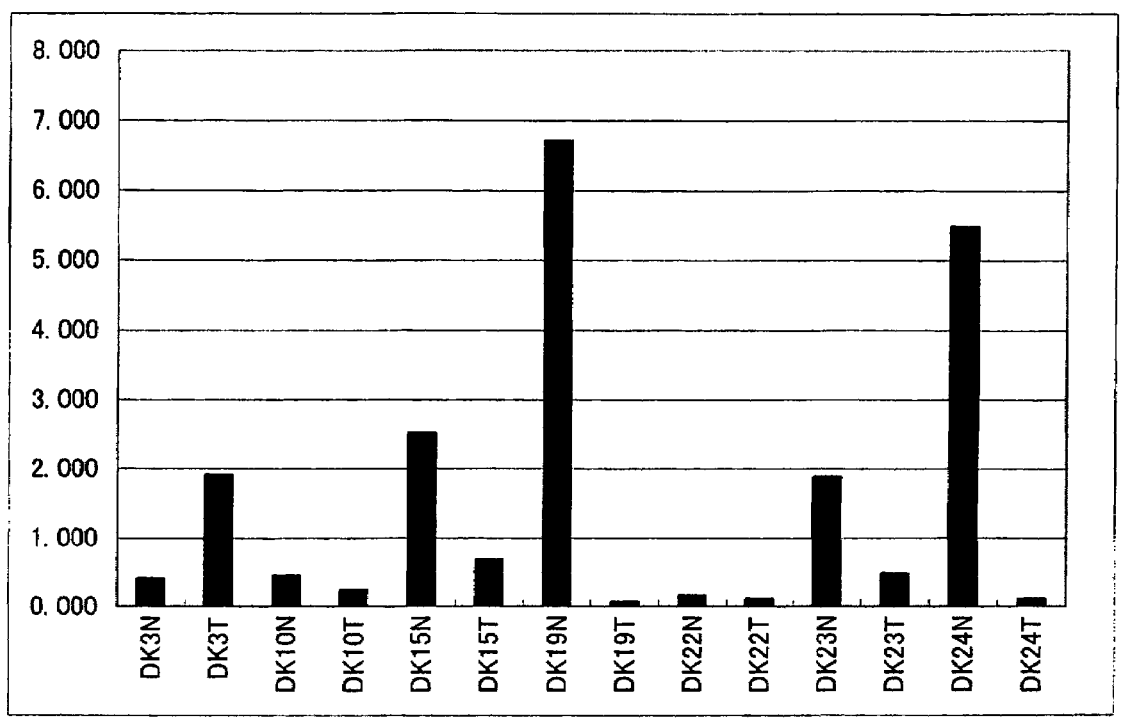
FIG. 4 shows comparison of the amount of expression of the gene according to the present invention in normal tissues and that in cancer tissues of colon cancer patients.

9. Expression of β3GnT-7 Gene in Normal Tissues and Cancer Tissues of Colon Cancer Patients The expression amounts of β3GnT-7 in normal (N)-tissues and cancer (T) tissues of actual colon cancer (DK) patients were measured by the method described in "8. Analysis of Tissue-specific Expression of β3GnT-7". The results are shown in FIG. 4. From these results, in samples except for DK3, that is, in samples of DK10, DK15, DK19, DK22 and DK23, the tendency that expression of β3GnT-7 in cancer tissue is smaller than in the normal tissue was observed.

The invention claimed is:

1. An isolated protein having an amino acid sequence shown in SEQ ID NO: 1, or an amino acid sequence having a homology of not less than 95% to the amino acid sequence of SEQ ID NO:1, which has an activity to transfer N-acetylglucosamine to a non-reducing terminal of Galβ1-4Glc or Galβ1-4GlcNAc group through β1,3-linkage.

2. The protein according to claim 1, which has the amino acid sequence shown in SEQ ID NO: 3, or wherein the amino acid sequence has a homology of not less than 95% to said amino acid sequence shown in SEO ID NO:3.

3. The protein according to claim 2, which has the amino acid sequence shown in SEQ ID NO:3.

4. A protein comprising the amino acid sequence recited in claim 1 or claim 2, which has an activity to transfer N-acetylglucosamine to a non-reducing terminal of Galβ1-4Glc or Galβ1-4GlcNAc group through β1,3-linkage.

5. A method for diagnosis of a cancer and/or tumor, comprising determining the amount of said protein according to claim 3, in (a) sample cell(s) separated from body.

6. The method according to claim 5, wherein said sample cell(s) is(are) originated from a digestive organ, and wherein said method is for diagnosis of a cancer and/or tumor of the digestive organ.

7. The method according to claim 6, wherein said sample cell(s) is(are) originated from colon, and wherein said method is for diagnosis of colon cancer.

* * * * *